United States Patent
Jin et al.

(10) Patent No.: US 9,623,151 B2
(45) Date of Patent: Apr. 18, 2017

(54) BIOMATERIALS AND IMPLANTS FOR ENHANCED CARTILAGE FORMATION, AND METHODS FOR MAKING AND USING THEM

(71) Applicant: THE REGENTS OF THE UNIVERSITY OF CALIFORNIA, Oakland, CA (US)

(72) Inventors: Sungho Jin, San Diego, CA (US); Seunghan Oh, Jeonju (KR); Karla Khalifa, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 50 days.

(21) Appl. No.: 14/341,831

(22) Filed: Jul. 27, 2014

(65) Prior Publication Data

US 2014/0335145 A1    Nov. 13, 2014

Related U.S. Application Data

(63) Continuation of application No. 12/997,689, filed as application No. PCT/US2009/049523 on Jul. 2, 2009, now abandoned.

(60) Provisional application No. 61/078,141, filed on Jul. 3, 2008, provisional application No. 61/087,957, filed on Aug. 11, 2008.

(51) Int. Cl.

| | | |
|---|---|---|
| *A61L 27/54* | (2006.01) | |
| *A61K 35/32* | (2015.01) | |
| *A61K 38/18* | (2006.01) | |
| *A61K 31/7088* | (2006.01) | |
| *A61K 9/127* | (2006.01) | |
| *A61L 27/02* | (2006.01) | |
| *C12N 5/077* | (2010.01) | |
| *B23K 15/00* | (2006.01) | |
| *B23K 26/20* | (2014.01) | |
| *H05B 6/02* | (2006.01) | |
| *A61L 27/06* | (2006.01) | |
| *A61L 27/38* | (2006.01) | |
| *C12M 1/12* | (2006.01) | |

(52) U.S. Cl.
CPC .............. *A61L 27/54* (2013.01); *A61K 9/127* (2013.01); *A61K 31/7088* (2013.01); *A61K 35/32* (2013.01); *A61K 38/1808* (2013.01); *A61K 38/1825* (2013.01); *A61K 38/1841* (2013.01); *A61K 38/1866* (2013.01); *A61K 38/1875* (2013.01); *A61L 27/025* (2013.01); *A61L 27/06* (2013.01); *A61L 27/3817* (2013.01); *A61L 27/3834* (2013.01); *A61L 27/3843* (2013.01); *B23K 15/0046* (2013.01); *B23K 26/20* (2013.01); *C12M 25/00* (2013.01); *C12N 5/0655* (2013.01); *H05B 6/02* (2013.01); *A61L 2300/414* (2013.01); *A61L 2300/602* (2013.01); *A61L 2300/626* (2013.01); *A61L 2300/64* (2013.01); *A61L 2400/12* (2013.01); *A61L 2430/06* (2013.01)

(58) Field of Classification Search
CPC ...... A61L 27/54; A61K 9/127; B23K 15/0046
See application file for complete search history.

(56) References Cited

U.S. PATENT DOCUMENTS

| 8,414,908 B2 | 4/2013 | Jin et al. |
| 8,906,402 B2 | 12/2014 | Webster et al. |
| 2010/0303716 A1 | 12/2010 | Jin et al. |

FOREIGN PATENT DOCUMENTS

| WO | 2006116752 A2 | 11/2006 | |
| WO | WO2006/116752 | * 11/2006 | ............... A61F 2/02 |
| WO | 2008066965 A3 | 6/2008 | |
| WO | 2009064964 A2 | 5/2009 | |
| WO | 2010003062 A3 | 1/2010 | |

OTHER PUBLICATIONS

Frenkel et al., "Scaffolds for Articular Cartilage Repair", Annals of Biomedical Engineering, vol. 32, No. 1, Jan. 2004, pp. 26-34.
Giffo-Schmitt, International Preliminary Report on Patentability, The International Bureau of WIPO, PCT Application No. PCT/US2009/049523, Jan. 5, 2011.
Li et al., "Electrospun silk-BMP-2 scaffolds for bone tissue engineering", Biomaterials, 2006:27, 3115-3124.
Yang, International Search Report, Korean Intellectual Property Office, PCT Application No. PCT/US2009/049523, Jan. 15, 2010.

* cited by examiner

*Primary Examiner* — Scott Long
(74) *Attorney, Agent, or Firm* — Greer, Burns & Crain, Ltd.; Gregory P. Einhorn

(57) ABSTRACT

The invention provides products of manufacture, e.g., biomaterials and implants, for cartilage maintenance and/or formation in-vivo, in-vitro, and ex-vivo, using nanotechnology, e.g., using nanotube, nanowire, nanopillar and/or nanodepots configured on surface structures of the products of manufacture.

21 Claims, 27 Drawing Sheets

BIOMATERIALS AND IMPLANTS FOR ENHANCED CARTILAGE FORMATION, AND METHODS FOR MAKING AND USING THEM

CROSS-REFERENCE TO RELATED APPLICATIONS

This United States utility patent application is a Continuation of U.S. patent application Ser. No. 12/997,689, filed Mar. 9, 2011 (now pending), which is a §371 national phase of PCT international patent application no. PCT/US2009/049523, having an international filing date of Jul. 2, 2009, which claims benefit of priority to U.S. Provisional Patent Application Ser. No. 61/078,141, filed Jul. 3, 2008, and U.S. Ser. No. 61/087,957, filed Aug. 11, 2008. The aforementioned applications are expressly incorporated herein by reference in their entirety and for all purposes.

TECHNICAL FIELD

This invention relates to the fields of nanotechnology, tissue engineering and regenerative medicine, and in alternative embodiments, the present invention provides biomaterials and implants for cartilage maintenance and/or formation in-vivo, in-vitro, and ex-vivo, using nanotechnology, e.g., using nanotube or nanopillar configured surface structures.

BACKGROUND

Cartilage defects are a main issue in orthopedics to which there is no known physiological treatment to restore the identical tissue. Because of the ever increasing elderly population with osteoarthritic disease and an estimated 1 million or more total joint arthroplasties performed annually in the United States, cartilage defects remain a major concern in orthopedics and there is a strong need to resolve this cartilage repair problem.

Cartilage tissue engineering remains a challenge because cartilage does not heal itself spontaneously as it does not contain blood vessels. The main cells of cartilage, chondrocytes, are limited in self repair. The low density of cells, which do not replicate, hide among a dense isolating extracellular matrix. This leads to a lack of regeneration ability because the cells are cut off from each other, other body tissues, and nutritive sources such as blood supply, and the usual inflammation response is absent.

Currently, treatments for cartilage repair are less than satisfactory, and rarely restore the necessary function nor return the tissue to its native normal state. Artificial cartilage prepared from cultured chondrocytes offers promise as a treatment for cartilage defects, but connecting this artificial soft tissue to bone in the attempts to restore the defected cartilage is difficult.

In the attempts to replace cartilage, most research involves the combination of in vitro expansion of chondrocytes with three-dimensional (3-D) synthetic or natural polymer scaffolds. Constructs have been comprised of materials such as polyglycolic acid, polylactic acid, various co-polymers, as well as natural materials of polysaccharides and collagen, and extracellular matrix proteins and hyaluronic acid constructs to mimic the natural in vivo environment.

Although the response of chondrocytes to these polymeric chemical constructs provided valuable information to advance the repair of chondral lesions, there are still complications to overcome. Problems have occurred such as acidic by product accumulation, local or systemic inflammatory reaction during in vivo degradation, and the degradation time is too short to allow neocartilage formation, leaving polymers less promising in clinical application. Furthermore, most of the polymers are lacking the dual functionality of osseointegration and cartilage growth, and do not always provide suitable mechanical properties needed to fully integrate with native bone tissue.

SUMMARY

The invention provides compositions and methods for maintaining and/or replacing damaged, injured or degenerated cartilage injury, lesions and defects with new cartilage, and to reduce the pain and dysfunction associated with cartilage injury, lesions and defects. The compositions and methods of the invention can be used as (or with) osteochondral autografts, osteocyte allografts, and autologous or allogenic chondrocyte implantations, including any techniques used for replacing or repairing cartilage.

The compositions and methods of the invention can be used with any type of metallic or ceramic biocompatible constructs, configuration and/or biomaterial design to optimize chondrocyte culture to successfully reproduce cartilage. In alternative aspects, the chondrocytes used to practice this invention include any cell that can produce and maintain the cartilaginous matrix, including osteochondrogenic cells and immature chondrocytes, e.g., chondroblasts, and more mature and/or differentiated forms, e.g., hypertrophic chondrocytes.

This invention provides novel nanostructured biomaterials, devices comprising such biomaterials, and fabrication methods for efficient reproduction of cartilage in human and animal body. The biomaterials of the invention can be used to initiate and/or accelerate chondrocyte cell growth and cartilage formation; and in alternative embodiments, release growth factors and other chemical or biological materials, e.g., as materials stored in a nano-depot of the nanostructured biomaterial surfaces of this invention. In alternative embodiments, by releasing growth factors and other chemical or biological materials, compositions and methods of the invention can be used to ameliorate local or systemic inflammatory reaction that slow or inhibit cartilage regeneration or repair, e.g., slow or inhibit local or systemic inflammatory reactions causing in vivo cartilage degradation.

This invention provides compositions and methods for building a cartilage, including e.g., a cartilage construction technique which in alternatively embodiments can be enhanced by incorporating (comprising) a stem cell, e.g., a mesenchymal stem cell, an adult stem cell and/or an embryonic stem cell, a pluripotent stem cell, an induced pluripotent stem cell (abbreviated as iPS cell or iPSC), a multipotent progenitor cell and/or a totipotent cell. In one embodiment, these stem cells are mammalian, e.g., human, stem cells. In alternative embodiments, nanostructures of the invention are utilized to improve the differentiation of stem cells (e.g., adult stem cells, iPS cells and/or embryonic stem cells) towards formation, adhesion and growth of chondrocytes, which is important for cartilage growth.

The invention provides products of manufacture comprising:

wherein optionally the product of manufacture is a cell-, cartilage- and/or bone growth-enhancing or cell differentiation-enhancing product of manufacture, or a bone- or cartilage-maintaining and/or bone or cartilage growth-enhancing product of manufacture, or an implant, (a) nanostructures comprising a nanotube, nanowire, nanopore, nanoribbon and/or a nanopillar surface configuration on a Ti and/or Ti-comprising alloy, or on a Ti-coated or Ti alloy-coated surface, or on a $TiO_2$ and/or $TiO_2$ alloy surface or coating, wherein the Ti and/or Ti-comprising alloy or the $TiO_2$ and/or $TiO_2$ alloy surface or coating, or the Ti-coated or Ti alloy-coated surface, comprises one or more surfaces (or a subsurface or a partial surface) of the product of manufacture, wherein optionally the nanostructures (nanotubes, nanowires, nanopores, nanoribbons and/or nanopillars) comprise a metal and/or a metal alloy comprising a Ti, a Zr, a Hf, a Nb, a Ta, a Mo and/or a W, or an oxide of a Ti, a Zr, a Hf, a Nb, a Ta, a Mo and/or a W, wherein optionally the nanostructures (nanotubes, nanowires, nanopores, nanoribbons and/or nanopillars) are formed directly and/or indirectly on and/or attached to a Ti surface and/or a Ti-coated surface, or Ti oxide surface and/or a Ti oxide-coated surface, wherein optionally the nanotubes have a diameter dimension in the range of between about 30 to 600 nm outside diameter, or between about 50 to 400 nm diameter, or between about 70 to 200 nm diameter, and/or optionally a height dimension in the range of between about 30 to 10,000 nm, and/or optionally between about 200 to 2,000 nm thickness, or between about 200 to 500 nm thickness, wherein optionally the Ti surface and/or Ti-coated surface, or Ti oxide surface and/or a Ti oxide-coated surface, comprises: the surface of a wire or microwire; the surface of a springy and/or a hairy wire or microwire; the surface of a mesh or mesh screen; the surface of an implant; a "pre-patterned" and/or a "pre-etched" surface made by machining or mask patterning and/or etching of the surface of the product of manufacture structure, wherein optionally the three-dimensional Ti wire or microwire is between about 10 to 100 µm in diameter and/or the Ti wire or microwire is a springy and compliant wire or microwire, wherein optionally the material used for the three-dimensional springy, coil, wire, or mesh screen scaffold comprises at least one of a metal or an alloy selected from the group consisting of Ti, Zr, Hf, Nb, Ta, Mo and W, or an alloy or an oxide or a mixture thereof, or stainless steel, or a Co—Cr—Ni—Mo alloy (commonly known as MP35N alloy), wherein the surface of the springy wire scaffold contains vertically configured nanotube or nanopore arrays with about 30 to 600 nm diameter, preferably 70 to 200 nm diameter, and about 200 to 2,000 nm thickness, and preferably 200 to 500 nm thickness, wherein optionally the Ti or Ti oxide alloy or Ti or Ti oxide on the Ti-coated, or Ti oxide-coated or Ti alloy-coated surface is between about 100 to 2000 µm thick; and wherein optionally the product of manufacture structure of (a) comprises (i) oxides of alloys comprising Ti or a Ti oxide or a $TiO_2$ by at least about 5%, 10%, 20%, 30%, 40%, 50%, 60%, 70%, 80% or 90% or more in weight %, or (ii) oxides of alloys comprising Zr, Hf, Nb, Ta, Mo, W, by at least about 5%, 10%, 20%, 30%, 40%, 50%, 60%, 70%, 80% or 90% or more weight %, or (ii) a ceramic, a polymer, a plastic, a Si-comprising composition, a Au-comprising composition, a Pd-comprising composition, a Pt-comprising composition, or a stainless steel;

(b) the product of manufacture of (a), and further comprising a chondrocyte, a stem cell, a totipotent cell, a multipotent progenitor cell and/or a pluripotent cell, wherein the chondrocyte functionality, as indicated by the degree of extracellular matrix formation, is increased by at least about 5%, 10%, 20%, 30%, 40%, 50%, 60%, 70%, 80% or 90% or more, as compared with the identical material but without the $TiO_2$ nanotube or nanopillar surface configuration;

(c) the product of manufacture of (a) or (b), further comprising a chondrocyte, a colony-forming unit-fibroblast (CFU-F), a marrow stromal cell or mesenchymal stem cell (MSC), a stem cell, a totipotent cell, a multipotent progenitor cell and/or a pluripotent cell, wherein optionally the cell is implanted in, seeded in or placed in the product of manufacture in-vivo, in-vitro, and/or ex-vivo;

(d) the product of manufacture of (b) or (c), wherein the stem cell is a mesenchymal stem cell (MSC), an adult stem cell, an induced pluripotent stem cell (abbreviated as iPS cell or iPSC) and/or an embryonic stem cell;

(e) the product of manufacture of any of (b) to (d), wherein the chondrocyte is an autologous chondrocyte, a hypertrophic chondrocyte, or a human chondrocyte;

(f) the product of manufacture of any of (a) to (d), further comprising on the surface of the product of manufacture a nano-depot, a microcavity and/or a macrocavity comprising a cell, a drug and/or a biological agent, wherein optionally the nanotube or a nanopillar, or microcavity and/or a macrocavity, acts as a depot or storage area comprising a cell, a drug and/or a biological agent, wherein optionally the microcavity has an entrance dimension of between about 1 to 100 micrometer, or a macrocavity having an entrance dimension of between about 100 to 1,000 micrometer; or (g) the product of manufacture of any of (a) to (f), having a structure as illustrated in any one of FIGS. 16 to 29.

In alternative embodiments of the products of manufacture of the invention, the product of manufacture comprises (a) a thin coating of a metal, a metal oxide, and/or an alloy at least about 1, 2, 3, 4, 5, 10, 15 nm, 20 nm, 30 nm, 40 nm, 50 nm, 60 nm, 70 nm, 80 nm, 90 nm or 100 nm or more nm in thickness at the surface, and/or (b) at least a portion of the surface underneath comprises a vertically aligned and adhering nanotube, nanoribbon, nanowire and/or nanopillar array structure or structures, and/or a plurality of recessed nanopore structures.

In alternative embodiments of the products of manufacture of the invention, the entrance dimension of the nano-depot, nanotube and/or nanopore is reduced (constricted or impeded) by a selective deposition of a metal or an alloy, a metal oxide and/or alloy oxide, and/or another compound, to induce a partial bottlenecking (constricting) configuration to slow down or impede the release rate of a compound or a substance stored in the nano-depot, nanotube and/or nanopore, wherein optionally the compound or substance comprises a drug and/or a biological agent stored in the nano-depot, nanotube and/or nanopore, wherein optionally the slowing down or impeding of the release rate of the compound or a substance stored in the nano-depot, nanotube and/or nanopore is at least by a factor of 2 or 3 or slower, or at least by a factor of about 10 or slower, than the case of non-bottlenecked (non-constricted) structure, wherein optionally the other compound used to partially bottleneck (constrict or impeded) the nano-depot and/or nanopore comprises a nitride, a fluoride, a carbide and/or a polymer material, wherein optionally the product of manufacture surface has a multiplex and/or a duplex distribution of nanostructure structures with different dimensions such that the product of manufacture comprises both one or more nano-depot, nanotube and/or nanopore structures having bottle-necked (constricted or impeded) pore structures together with nano-depot, nanotube and/or nanopore structures which do not have the bottleneck diameter (constricted or impeded opening) reductions, wherein optionally the relative area fraction of bottle necked (constricted or impeded opening) nano-depot, nanotube and/or nanopore structures in the product of manufacture is in the range of about 2% to 50% of the total available surface area of the product of manufacture, or in the range of about 2% to 50% of the total available surface area available for stimulating cell growth, cartilage growth and/or bone deposition.

In alternative embodiments of the products of manufacture of the invention, the product of manufacture further comprises a chemical, a drug and/or a biological agent, and optionally the chemical, drug and/or biological agent comprises a small molecule, a growth factor, a collagen, a protein, a biomolecule, a gene, a nucleic acid, an RNA or a DNA, a nucleic acid expression vector, an antibiotic, a hormone, a therapeutic drug, a functional particle, a liposome, or a magnetic, metallic, ceramic or a polymer particle; or, a differentiation-inducing chemical, drug and/or biomolecule, and optionally the chemical, drug and/or biological agent is attached to or coated on the product of manufacture, or is stored in a nanopore, nanodepot and/or nanotube, or the chemical, drug and/or biological agent is attached to, coated on or stored between nanostructures comprising a plurality of nanopillars, nanotubes, nanowires and/or nanoribbons, and optionally the chemical, drug and/or biological agent comprises (are) a fibroblast growth factor (FGF), an epidermal growth factor (EGF), a vascular endothelial growth factor (VEGF), a transforming growth factor beta-1 (TGF-β1) or a transforming growth factor beta-2 (TGF-β2), a bone morphogenic protein (BMP), an agent that stimulates chondrocyte growth, maintenance and/or differentiation, a chemical or biomolecule osteogenic-inducing agent, a fibroblast growth factor and/or a vascular endothelial growth factor, a bisphosphonate, a chemical agent that suppresses the bone loss by suppressing osteoclasts (the type of bone cell that breaks down bone tissue), wherein optionally the chemical, drug and/or biological agent are positioned on the side of an implant surface intended for cartilage growth and comprise (are) chondrogenic inducing agents, and/or a chemical or a biomolecule-comprising agent that stimulates chondrocyte growth, maintenance and/or differentiation;

and optionally a biological agent positioned on another or opposite side of the implant surface is intended for bone growth and optionally comprises a chemical, drug and/or biological agent that stimulates or maintains bone growth; or (c) the product of manufacture of (b), wherein the bone morphogenic protein (BMP) is (or comprises) bone morphogenetic protein 2 (BMP-2), bone morphogenetic protein 3 (BMP-3), bone morphogenetic protein 4 (BMP-5), bone morphogenetic protein 5 (BMP-5), bone morphogenetic protein 6 (BMP-6), bone morphogenetic protein 7 (BMP-7), bone morphogenetic protein 8 (BMP-8a), bone morphogenetic protein 10 (BMP-10), bone morphogenetic protein 15 (BMP-15).

In alternative embodiments, the products of manufacture of the invention comprise functional particles comprising e.g., magnetic oxide particles or metallic particles utilized for remotely actuated RF heating and creation of temperature gradient for accelerated or switch-on, or switch-off release of the chemical, drug and/or biological agent stored in the nanopore, nanodepot and/or nanotube space.

The invention provides methods of fabricating a chondrocyte attachment-enhancing and/or chondrocyte growth-enhancing product of manufacture comprising a nanotube, nanowire, nanopore and/or nanopillar configuration comprising:

(a) use of anodization, formation and selective phase removal of a two-phase mask layer using diblock copolymer layer, spinodally decomposing alloy layer, or two-phased alloy film, followed by selective etching of a biomaterial surface to produce a nanotube or nanopillar surface configuration on a surface of the product of manufacture;

(b) spot-welding, or induction melting-bonding, or electron-beam ("e-beam") bonding, or laser bonding, or braze-bonding, a plurality of nanotubes or nanowires onto a $TiO_2$ base on a surface of the product of manufacture, wherein the base comprises: a Ti, Zr, Hf, Nb, Ta, Mo or W; or a Ti alloy or oxide, a $TiO_2$, an Au or Au oxide, a Pt or Pt oxide, a Pd or a Pd oxide; a mixture comprising an alloy or an oxide of one or more of Ti, Au, Pt or Pd; or, an oxide of an alloy comprising Zr, Hf, Nb, Ta, Mo or W;

(c) fabricating on the base surface of the product of manufacture a nanotube, nanopore and/or nanopillar configuration, wherein the base comprises a bulk metal or alloy, deposited thin film or deposited thick layer selected from: a Ti, Zr, Hf, Nb, Ta, Mo or W; or a Ti alloy comprising Ti, Al, and V, or Ti alloy one or more of Ti, Au, Pt or Pd; or, an alloy comprising Zr, Hf, Nb, Ta, Mo or W;

(d) the method of any of (a) to (c), wherein the product of manufacture comprises a surface having a duplex distribution of the nanostructure dimensions such that a nanopore or nano-depot has an intentionally bottle-necked or constricted pore structure or opening, wherein optionally the bottle-necked or constricted pore structure or opening results in a slower release of a stored agent or composition, and optionally the agent or composition comprises a drug and/or a biological agent, and optionally nanostructure with bottle-necked or constricted pore structures or openings are mixed and distributed together with regular (non-bottle-necked or non-constricted pore structures or openings) nanotubes or nanopores (which do not have the bottleneck diameter reduction), and optionally the relative area fraction of the bottle necked agent or composition release region is in the range of about 2% to 50% of the total available surface area of the product of manufacture, or in the range of about 2% to 50% of the total available surface area available for cartilage and/or bone growth or attachments, wherein optionally the product of manufacture comprises a configuration as illustrated in FIG. 13; or (e) the method of any of (a) to (d), wherein the product of manufacture comprises a product of manufacture composition of the invention, or the product of manufacture has a structure as illustrated in any one of FIGS. 5, 13 and 16 to 29.

The invention provides methods of fabricating a product of manufacture comprising a macroscale added-on scaffold structure for 3-dimensional cartilage construction using protruding springy wires, mesh screens, vertical pillar array columns, comprising (i) (a) attaching or forming a plurality of space-containing and/or springy protruding surface scaffold structures for three-dimensional chondrocyte assembly and cartilage growth, wherein optionally space-containing and/or springy protruding surface scaffold structures are attached or formed on a surface of the product of manufacture by spot-welding, or induction melting-bonding, or electron-beam ("e-beam") bonding, or laser bonding, or braze-bonding of a plurality of wires coils, mesh screens onto a surface of the product of manufacture, wherein optionally the material used for the three-dimensional springy, coil, wire, or mesh screen scaffold comprises a metal or an alloy or an oxide thereof selected from Ti, Zr, Hf, Nb, Ta, Mo or W, or an alloy or an oxide comprising at least one of these elements, or a stainless steel, or a Co- or Cr-comprising alloy, or a Co—Cr—Ni—Mo alloy, wherein optionally the wire diameter in the range of between about 10 to 100 um, wherein optionally the wires in the attached three-dimensional scaffold have a surface structure of either nanotubes or nanopores having diameter in the range of between about 30 to 600 nm, or between about 70 to 200 nm, wherein optionally the wires in the attached three-dimensional scaffold have a thickness of between about 300 to 400 nm, between about 200 to 500 nm, to between about 100 to 600 nm, wherein the material used for the three-dimensional springy, coil, wire, or mesh screen scaffold comprises a metal or alloy selected from Ti, Zr, Hf, Nb, Ta, Mo or W, or alloys containing at least one of these elements, or stainless steel, or Co—Cr—Ni—Mo alloy (commonly known as MP35N alloy), wherein the surface of the springy wire scaffold contains vertically configured nanotube or nanopore arrays with about 30 to 600 nm diameter, preferably 70 to 200 nm diameter, and about 200 to 2,000 nm thickness, and preferably 200 to 500 nm thickness, wherein a base material onto which the springy three-dimensional metal scaffold is attached comprises a bulk metal or alloy, deposited thin film or deposited thick layer selected from: a Ti, Zr, Hf, Nb, Ta, Mo or W; or a Ti alloy comprising Ti, Al, and V, or Ti alloy one or more of Ti, Au, Pt or Pd; or, an alloy comprising Zr, Hf, Nb, Ta, Mo or W, (ii) the method of (i), further comprising introducing a chondrocyte-growth-enhancing nanostructure on the surface of the three-dimensional scaffold wire or pillar surface by use of anodization, formation and selective phase removal of a two-phase mask layer using diblock copolymer layer, spinodally decomposing alloy layer, or two-phased alloy film, followed by selective etching of a biomaterial surface to produce a nanotube or nanopillar surface configuration; or (iii) the method of (i) or (ii), wherein the product of manufacture comprises a composition of the invention, and/or a product of manufacture made by a method of the invention, or the product of manufacture has a structure as illustrated in any one of FIGS. 5, 13 and 16 to 29.

The invention provides uses of a product of manufacture of the invention, or a product of manufacture made by a method of the invention, wherein the use comprises restoration, restructuring or repair of cartilage tissue in a thumb, a fingers, a wrist, an elbow, a shoulder, a hip, a knee, an ankle, a foot, a toe, an inter-vertebral disc of the spinal cord or a rib cage, or a nose or an ear, or a method of restoration or restructuring or repair of cartilage tissue in a thumb, a fingers, a wrist, an elbow, a shoulder, a hip, a knee, an ankle, a foot, a toe, an inter-vertebral disc of the spinal cord or a rib cage, or a nose or an ear, comprising use of the product of manufacture of the invention, wherein optionally the method or use comprises in vivo implantation of the product of manufacture of the invention.

The invention provides uses of a product of manufacture of the invention, or a product of manufacture made by a method of the invention, wherein the product of manufacture is used to enable joint movement while providing the structural support and chemical environment for new cartilage tissue to grow and fill defect, or to replace damaged, infected, aged, or diseased cartilage caused by various diseases such as arthritis, osteoarthritis, isolated femropatellar osteoarthritis, rheumatoid arthritis, chronic or systemic autoimmune disorder, lupus, or other autoimmune diseases, osteonecrosis of the joint, or septic arthritis caused by joint infection, or a method to enable joint movement while providing the structural support and chemical environment for new cartilage tissue to grow and fill defect, or to replace damaged, infected, aged, or diseased cartilage caused by various diseases such as arthritis, osteoarthritis, isolated femropatellar osteoarthritis, rheumatoid arthritis, chronic or systemic autoimmune disorder, lupus, or other autoimmune diseases, osteonecrosis of the joint, or septic arthritis caused by joint infection, comprising use of the product of manufacture of the invention, or a product of manufacture made by a method of the invention, wherein optionally the method or use comprises in vivo implantation of the product of manufacture of the invention, or a product of manufacture made by a method of the invention.

The invention provides in vivo uses of a product of manufacture of the invention, or a product of manufacture made by a method of the invention, wherein the product of manufacture is applied in vivo as a patch bone implant piece, wherein optionally the product of manufacture serves a dual purpose of comprising at least one exposed surface that enhances a chondrocyte growth and cartilage formation while comprising another surface (e.g., an opposing surface or a bottom surface) facing the existing bone to induce a strong osseo-integration.

The invention provides implants, e.g., patch bone implant pieces, comprising a product of manufacture of the invention, or a product of manufacture made by a method of the invention, wherein optionally the product of manufacture serves a dual purpose of comprising at least one exposed surface that enhances a chondrocyte growth and cartilage formation while comprising another surface (e.g., an opposing surface or a bottom surface) facing the existing bone to induce a strong osseo-integration.

The invention provides in vivo uses of a product of manufacture of the invention, or a product of manufacture made by a method of the invention, wherein the product of manufacture comprises a patch implant comprising Ti, or a Ti alloy or Ti oxide or a mixture thereof, and optionally the patch implant is permanently screwed onto or into an existing bone or temporarily fixed onto or into an existing bone with strings or straps.

The invention provides implants, or bone implants, or patch implants, comprising a product of manufacture of the invention, or a product of manufacture made by a method of the invention, optionally comprising a Ti, a Ti alloy or $TiO_2$ or a mixture thereof.

The invention provides in vivo uses of a product of manufacture of the invention, or a product of manufacture made by a method of the invention, wherein the product of manufacture is utilized as a chondrocyte cell culture substrate for enhanced or new chondrocyte, stem cell and/or extracellular matrix production, or a method for enhancing chondrocyte, stem cell and/or extracellular matrix production or stimulating new chondrocyte, stem cell and/or extracellular matrix production comprising in vivo or ex vivo use of the product of manufacture of the invention. In alternative embodiments of uses or methods of the invention, wherein an individual's own chondrocyte cells are used (autologous cells are used), and the method optionally comprises implanting the product of manufacture into the individual (a human or an animal) near a cartilage damage regions or a tissue in need of repair and/or reconstruction.

The invention provides chondrocyte cell culture substrates for enhanced or new chondrocyte, stem cell and/or extracellular matrix production comprising a product of manufacture of the invention, or a product of manufacture made by a method of the invention.

The invention provides methods for making an implant comprising a cell, comprising:

(a) (i) providing a chondrocyte, a colony-forming unit-fibroblast (CFU-F), a marrow stromal cell (MSC), a stem cell, a totipotent cell, a multipotent progenitor cell and/or a pluripotent cell;

(ii) providing a product of manufacture of the invention, or a product of manufacture made by a method of the invention, wherein optionally the product of manufacture comprises a $TiO_2$-comprising nanotube, nanowire and/or nanopore; and (iii) adding the cell of (a) to the product of manufacture of (b) under cell culture conditions;

(b) the method of (a), wherein the stem cell is a mesenchymal stem cell, an adult stem cell, an induced pluripotent stem cell (abbreviated as iPS cell or iPSC) and/or an embryonic stem cell;

(c) the method of (a), wherein the product of manufacture is fabricated as a bone implant, or a patch implant, or patch bone implant piece;

(d) the method of any of (a) to (c), wherein the cell culture conditions comprise use of cell growth and/or cell differentiation factors;

(e) the method of (d), wherein the cell growth and/or cell differentiation factors comprise a drug or chemical or biological agent that promotes the growth, maintenance and/or regeneration of a cell;

(f) the method of (e) wherein the drug or chemical or biological agent that promotes the growth, maintenance and/or regeneration of a cell promotes the differentiation growth, maintenance and/or regeneration of a chondrocyte, a stem cell, a totipotent cell, a multipotent progenitor cell and/or a pluripotent cell;

(g) the method of (d), (e) or (f), wherein the cell growth, cell differentiation factor or biological agent comprises a chondrogenic agent or a bone morphogenic protein (BMP) or an agent, drug or chemical that stimulates chondrocyte growth, maintenance and/or differentiation, or a fibroblast growth factor and/or a vascular endothelial growth factor, and optionally the chondrogenic agent is placed on an implant surface region intended for cartilage growth, and optionally bone morphogenic protein (BMP) is placed on an implant surface region intended for bone growth, and optionally fibroblast growth factor and/or vascular endothelial growth factor are placed on an implant surface region intended for bone growth for osseointegration attachment to the existing bone structure;

(h) the method of (g), wherein the bone morphogenic protein (BMP) is (or comprises) a bone morphogenetic protein 2 (BMP-2), a bone morphogenetic protein 3 (BMP-3), a bone morphogenetic protein 4 (BMP-5), a bone morphogenetic protein 5 (BMP-5), a bone morphogenetic protein 6 (BMP-6), a bone morphogenetic protein 7 (BMP-7), a bone morphogenetic protein 8 (BMP-8a), a bone morphogenetic protein 10 (BMP-10), a bone morphogenetic protein 15 (BMP-15);

(i) the method of (g), wherein the wherein the drug or chemical or biological agent comprises a fibroblast growth factor (FGF), an epidermal growth factor (EGF), a vascular endothelial growth factor (VEGF), a transforming growth factor beta-1 (TGF-β1) or a transforming growth factor beta-2 (TGF-β2), a bone morphogenic protein (BMP) (e.g., an agent that stimulates chondrocyte growth, maintenance and/or differentiation), fibroblast growth factors and/or vascular endothelial growth factors (j) the method of any of (d) to (i), wherein cell growth, cell differentiation factor or biological agent comprises a recombinant protein, or an autologous protein, or a human protein;

(k) the method of any of (a) to (j), wherein the cell culture conditions comprise a chondrogenic-inducing media;

(l) the method of (k), wherein the chondrogenic-inducing media comprises one, several of all of: a serum-free DMEM, an ascorbate, a dexamethasone, L-proline, sodium pyruvate, ITS-plus, an antibiotic and/or a recombinant protein; or (m) the method of any of (a) to (l), wherein the cell is implanted in, seeded in or placed in the implant in-vivo, in-vitro, and/or ex-vivo.

The invention provides methods of fabricating chondrocyte-enhancing nanotube or nanopillar configurations using anodization, formation and selective phase removal of a two-phase mask layer using diblock copolymer layer, spinodally decomposing alloy layer, or two-phased alloy film, followed by selective etching of the biomaterial surface to produce nanotube or nanopillar surface configurations.

The invention provides uses of the product of manufacture of the invention, wherein the use comprises restoration, restructuring or repair of cartilage tissue in a thumb, a fingers, a wrist, an elbow, a shoulder, a hip, a knee, an ankle, a foot, a toe, an inter-vertebral disc of the spinal cord or a rib cage, or a nose or an ear. The invention provides methods of restoration or restructuring or repair of cartilage tissue in a thumb, a fingers, a wrist, an elbow, a shoulder, a hip, a knee, an ankle, a foot, a toe, an inter-vertebral disc of the spinal cord or a rib cage, or a nose or an ear, comprising use of the product of manufacture of this invention, wherein in one embodiment the use comprises in vivo implantation of a product of manufacture of this invention.

The invention provides uses of the product of manufacture of the invention, wherein the product of manufacture is used to enable joint movement while providing the structural support and chemical environment for new cartilage tissue to grow and fill defect, or to replace damaged, infected, aged, or diseased cartilage caused by various diseases such as arthritis, osteoarthritis, isolated femropatellar osteoarthritis, rheumatoid arthritis, chronic or systemic autoimmune disorder, lupus, or other autoimmune diseases, osteonecrosis of the joint, or septic arthritis caused by joint infection, or a method to enable joint movement while providing the structural support and chemical environment for new cartilage tissue to grow and fill defect, or to replace damaged, infected, aged, or diseased cartilage caused by various diseases such as arthritis, osteoarthritis, isolated femropatellar osteoarthritis, rheumatoid arthritis, chronic or systemic autoimmune disorder, lupus, or other autoimmune diseases, osteonecrosis of the joint, or septic arthritis caused by joint infection, comprising use of the product of manufacture of any of this invention, wherein optionally the method or use comprises in vivo implantation of the product of manufacture of any of this invention.

The invention provides uses of the product of manufacture of the invention, wherein the product of manufacture is applied as an implant, or a bone implant, or a patch implant patch bone, wherein the implant surfaces serve dual/multiple purposes; for example having more than one (e.g., two or more) surfaces with multiple purposes, e.g., one surface for cartilage growth and another surface of the implant for bone growth. For example, implant surfaces can serve dual/multiple purposes—where one (e.g., can be described as "exposed") implant surface enhances chondrocyte growth and cartilage formation while another surface, e.g., the opposite (e.g., non-exposed) surface of the implant, or one or more implant surfaces intended for bone growth, or the one or more implant surfaces facing the existing bone, induce (or are designed to induce or stimulate) bone growth and/or strong osseo-integration.

The invention provides an in-vivo use of the product of manufacture of the product of manufacture of the invention, wherein the product of manufacture is applied as an implant, or a bone implant, or a patch implant, or patch bone implant piece, wherein in alternative embodiments the product of manufacture serves a dual or multiple purposes, e.g., comprising one or more exposed surface(s) that enhance(s) chondrocyte growth and cartilage formation while another (one or more) surface(s) facing the existing bone to induce bone growth and/or a strong osseo-integration. For example, in alternative embodiments, the invention provides an implant, or a bone implant, or a patch implant, or patch bone implant piece comprising any product of manufacture of the invention, wherein in alternative embodiments the product of manufacture serves a dual or multiple purposes comprising enhancing chondrocyte growth and cartilage formation on one or more surfaces (e.g., exposed surfaces) and also comprising another surface, e.g., the opposite (e.g., non-exposed) surface of the implant, or one or more implant surfaces intended for bone growth, or one or more implant surfaces facing the existing bone to induce bone growth and/or a strong osseo-integration.

The invention provides an in-vivo use of the product of manufacture of the invention, wherein the product of manufacture comprises a patch implant is made of Ti, and is permanently screwed onto the existing bone or temporarily fixed with strings or straps. The invention provides a patch implant comprising a product of manufacture of the invention, optionally comprising Ti or $TiO_2$.

The invention provides in-vivo use of the product of manufacture of the invention, wherein the product of manufacture is utilized as a chondrocyte cell culture substrate for enhanced or new chondrocyte, stem cell and/or extracellular matrix production, or a method for enhancing chondrocyte, stem cell and/or extracellular matrix production or stimulating new chondrocyte, stem cell and/or extracellular matrix production comprising in-vivo use of the product of manufacture of the invention. In alternative embodiments of the use or method an individual's own chondrocyte cells are used (autologous cells are used), optionally followed by implanting the product of manufacture into the individual (a human or an animal) near a cartilage damage regions or a tissue in need of repair and/or reconstruction.

In one aspect of uses of compositions and methods of the invention, an individual's own chondrocyte or other cells are used (e.g., chondrocytes and fibroblasts, osteoclasts or osteoblasts), followed by implanting into a human or an animal near a cartilage damage regions or a tissue in need of repair and/or reconstruction.

The invention provides methods for making an implant (an implant for an individual, e.g., human or animal) comprising a cell (or a plurality of cells), comprising:

(a) (i) providing a chondrocyte, a colony-forming unit-fibroblast (CFU-F), a marrow stromal cell or mesenchymal stem cell (MSC), a stem cell, a totipotent cell, a multipotent progenitor cell and/or a pluripotent cell, wherein optionally the cell is implanted in, seeded in or placed in the implant in-vivo, in-vitro, and/or ex-vivo;

(ii) providing a product of manufacture of the invention, wherein optionally the product of manufacture comprises a $TiO_2$-comprising nanotube, nanowire and/or nanopore; and (iii) adding the cell of (a) to the product of manufacture of (b) under cell culture conditions;

(b) the method of (a), wherein the stem cell is a mesenchymal stem cell, an adult stem cell, an induced pluripotent stem cell (abbreviated as iPS cell or iPSC) and/or an embryonic stem cell;

(c) the method of (a), wherein the product of manufacture is fabricated as a bone implant, or a patch implant, or patch bone implant piece;

(d) the method of any of (a) to (c), wherein the cell culture conditions comprise use of cell growth and/or cell differentiation factors;

(e) the method of (d), wherein the cell growth and/or cell differentiation factors comprise a biological agent that promotes the growth, maintenance and/or regeneration of a cell;

(f) the method of (e) wherein the biological agent that promotes the growth, maintenance and/or regeneration of a cell promotes the differentiation growth, maintenance and/or regeneration of a chondrocyte, a stem cell, a totipotent cell, a multipotent progenitor cell and/or a pluripotent cell;

(g) the method of (d), (e) or (f), wherein the cell growth, cell differentiation factor or biological agent comprises a bone morphogenic protein (BMP) (e.g., an agent that stimulates chondrocyte growth, maintenance and/or differentiation), fibroblast growth factors and/or vascular endothelial growth factors;

(h) the method of (g), wherein the bone morphogenic protein (BMP) is (or comprises) a bone morphogenetic protein 2 (BMP-2), a bone morphogenetic protein 3 (BMP-3), a bone morphogenetic protein 4 (BMP-5), a bone morphogenetic protein 5 (BMP-5), a bone morphogenetic protein 6 (BMP-6), a bone morphogenetic protein 7 (BMP-7), a bone morphogenetic protein 8 (BMP-8a), a bone morphogenetic protein 10 (BMP-10), a bone morphogenetic protein 15 (BMP-15);

(i) the method of (g), wherein the wherein the biological agent comprises a fibroblast growth factor (FGF), an epidermal growth factor (EGF), a vascular endothelial growth factor (VEGF), a transforming growth factor beta-1 (TGF-β1) or a transforming growth factor beta-2 (TGF-β2), a bone morphogenic protein (BMP) (e.g., an agent that stimulates chondrocyte growth, maintenance and/or differentiation), fibroblast growth factors and/or vascular endothelial growth factors (j) the method of any of (d) to (i), wherein cell growth, cell differentiation factor or biological agent comprises a recombinant protein, or an autologous protein, or a human protein;

(k) the method of any of (a) to (i), wherein the cell culture conditions comprise a chondrogenic-inducing media;

(k) the method of (j), wherein the chondrogenic-inducing media comprises one, several of all of: a serum-free DMEM, an ascorbate, a dexamethasone, L-proline, sodium pyruvate, Insulin-Transferrin-Selenium (ITS) or ITS-PLUS™ (Gibco-Invitrogen, Carlsbad, Calif.), an antibiotic and/or a recombinant protein.

Also provided herein are kits comprising compositions of the invention including instructions for practicing the methods provided herein.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

FIG. 5(a) illustrates an exemplary nano-imprinting of masking resist, FIG. 5(b) illustrates an exemplary chemical or RIE etch to form Ti nanopillar array, which can be converted to $TiO_2$ nanopillars or Ti nanopillars with surface $TiO_2$ layer, FIG. 5(c) illustrates how this exemplary nanopillar construction can act as a guided and vertically aligned adhesion and growth matrix for cells and cartilage using e.g., Ti wires, pillars or columns, e.g., optionally having surface nanotubes; as described in detail, below.

FIG. 12(a): illustrates a low magnification comparing collagen shape on exemplary flat Ti vs 100 nm diameter nanotubes of the invention, FIG. 12(b): illustrates a higher magnification showing immunofluorescent images of collagen type II (red) and DAPI (blue) nuclear staining of BCCs on polystyrene, flat Ti, and 30, 50, 70, 100 nm $TiO_2$ surfaces after 5 days of culture; as described in detail, below.

FIG. 13(a) illustrates an exemplary embodiment including as-made $TiO_2$ nanotubes, FIG. 13(b) illustrates an exemplary embodiment where cells, drugs and/or biological agents stored in the nano-depots, FIG. 13(c) illustrates an exemplary embodiment comprising a diameter-reduced nano-depot entrance for slower release of stored cells, drugs and/or biological agents, FIG. 13(d) illustrates an exemplary embodiment comprising locally distributed bottlenecked regions within the regular nanotube region; as described in detail, below.

FIG. 14(a) illustrates an exemplary embodiment comprising a $TiO_2$ nano-pillar, FIG. 14(b) illustrates an exemplary embodiment comprising cells, drugs and/or biological agents stored in the gap between nanopillars, FIG. 14(c) illustrates an exemplary embodiment comprising a dimension reduced entrance for slower release of stored cells, drugs and/or biological agents from the nanopillar gap; as described in detail, below.

FIG. 15(a) an articular cartilage defect (the arrows illustrating the example cartilage defect and particular anatomical details of the illustrated knee, including the femur, articular cartilage, fibula, knee cap, the example cartilage defect and the tibia), FIG. 15(b) accelerated in vitro chondrocyte culture using an exemplary $TiO_2$ nanotube substrate of this invention (which in this example is used as a "scaffold" to repair the cartilage defect), FIG. 15(c) an injection of cultured chondrocytes to an in vivo implanted exemplary $TiO_2$ nanotube substrate "scaffold" to correct the cartilage defect (see arrow); as described in detail, below.

Like reference symbols in the various drawings indicate like elements.

DETAILED DESCRIPTION

Figure 1:
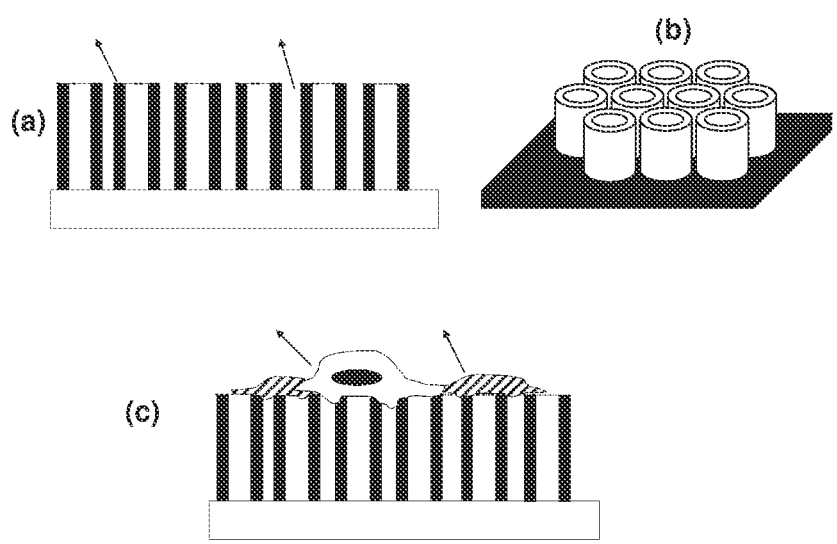
FIG. 1(a)-(c) schematically illustrates exemplary devices comprising self-organized $TiO_2$ nanotube arrays formed on titanium substrate to accelerate chondrocyte proliferation and cartilage formation as well as osteoblast cell proliferation and bone osseointegration according to the invention; as described in detail, below.

The invention provides products of manufacture, e.g., biomaterials and implants, for cartilage formation in-vivo, in-vitro, and ex-vivo, using nanotechnology, e.g., using nanotube or nanopillar configured surface structures.

In one embodiment, the invention provides products of manufacture comprising a dually functional substrate that supports the growth and attachment of cartilage tissue on one extremity and encourages osseointegration—a direct structural and functional connection to living bone—on the other. In one embodiment, the invention provides products of manufacture that provide an engineered interface between artificial cartilage and native bone.

In alternative embodiments, the compositions of the invention comprise cartilage-inducing substrate materials with the novel surface configurations of nanotubes and nanopillars of this invention. In one aspect, nanostructure, e.g., nanotubes and nanopillars, of this invention comprise Ti and Ti oxide (e.g., $TiO_2$) as well as alloys containing Ti or Ti oxide (e.g., $TiO_2$), e.g., at least about 5%, 10%, 20%, 30%, 40%, 50%, 60%, 70%, 80% or 90% or more weight %. In alternative embodiments, Ti oxide alloys and $TiO_2$ alloys used to practice this invention are oxides of an alloy comprising Ti and other metal(s), e.g., the oxide of the well known implant alloy like Ti-6% Al-4% V. For example, a Ti oxide alloy and/or an $TiO_2$ alloy used to practice this invention either have only (e.g., consist essentially of) Ti as a metal or have other (e.g., comprise) metal or metals, or another material, e.g., a ceramic or a carbon-based material.

In alternative embodiments, other related materials are used, e.g., such as Zr, Hf, Nb, Ta, Mo, W, and their oxides, or alloys of these metals and oxides, e.g., by at least 5%, 10%, 20%, 30%, 40%, 50%, 60%, 70%, 80% or 90% or more weight %. Other materials such as stainless steels, Si, Si oxide, carbon, diamond, noble metals (such as Au, Ag, Pt and their alloys), polymer or plastic materials, or composite metals, ceramics or polymers can also be utilized to produce and use similar desired surface configurations for bio implant and cell growth applications; alternative embodiments have a coating of nano-structured Ti and Ti oxide, Zr, Hf, Nb, Ta, Mo, W and/or their oxides, or their alloys, with a thickness of at least about 1, 2, 3, 4, 5, 10, 15, 20, 30, 40, 50, 60, 70, 80, 90 or 100 nm, and/or have a coating coverage of at least 5%, 10%, 20%, 30%, 40%, 50%, 60%, 70%, 80% or 90% or more of the total surfaces.

The invention provides materials, fabrication methods, and therapeutic applications of cartilage-inducing biomaterials substrate based on nanostructured surfaces, in particular, with Ti oxide based nanotube or nanopillar configurations. In alternative embodiments, the novel biomaterials are fabricated by anodization or nanomasked etching techniques to enable accelerated chondrocyte cell growth and cartilage formation, and to allow release of growth factors and other chemical or biological materials stored in the nano-depot of the nanostructured biomaterial surfaces. Other materials such as Ti alloy based oxides or containing Zr, Hf, Nb, Ta, Mo, W based oxides, or stainless steel based alloys are also utilized.

The chondrocyte growth enhancing nanotube or nanopillar configuration materials can also be in the form of thin coating of other metals or alloys, at least about 1, 2, 3, 4, 5, 10, 15, 20, 30, 40, 50, 60, 70, 80, 90 or 100 or more nm thick surface portions, which can be converted into a vertically aligned and adhering nanotube or nanopillar array structures.

The novel inventive cartilage-inducing biomaterials can be utilized for repair of articular cartilage of knee or finger bones, vertebral disks, and other cartilages, in the form of bone implant surface coatings to induce osseo-integration to existing bone on the contact side while inducing enhanced chondrocyte culture and cartilage formation on the exposed implant surface.

The inventive cartilage-inducing biomaterials can also be utilized as in vitro or ex vivo cell culture substrate for enhanced chondrocyte and extracellular matrix, followed by implanting into human or animal body.

Nano-depot configurations of the inventive biomaterials can also be utilized as a reservoir to store and slowly and continuously deliver growth factors, antibiotics, and other drugs and biochemicals for further therapeutic benefits for patients.

The invention provides improved biomaterials implants and substrates for enhanced cartilage formation, and novel techniques for fabricating such novel biomaterials, and various biological and therapeutic applications using such materials are disclosed. Referring to the drawings, FIGS. 1(a)-(c) schematically illustrate exemplary devices comprising self-organized $TiO_2$ based nanotube arrays grown on titanium metal or alloy substrate to accelerate chondrocyte cell proliferation according to the invention. In alternative embodiments, $TiO_2$ nanotubes or any other biocompatible nanotubes used in devices of the invention have dimensions of anywhere between about 10 to 1000 nm in diameter, or 30 to 300 nm, or 60 to 200 nm in diameter. In alternative embodiments, heights of the tubules are determined in part by the desired aspect ratio as relatively short height with an aspect ratio of less than 10, or less than 5, for reduced tendency for ease of storing and eventual dispensing of drugs or biological agents intentionally placed within the tubule cavity, as well as to reduce a possibility of long tubules in thick nanotube layers delaminating or breaking off and floating around in the human body. In alternative embodiments, heights can be between about 40 to 2000 nm, or 100 to 600 nm.

For some embodiments, a vertical alignment with an open top pore is crucial for bio implant and related applications; for example, FIG. 1(a) illustrates an exemplary nanotube construction of the invention having an open top, arrows illustrate and emphasize the spacing between nanotubes for fluid flow, and the parallel aligned three-dimensionally configured nanotube array, which in some embodiments comprise $TiO_2$ nanotubes; FIG. 1(b) illustrates how this exemplary nanotube construction of the invention allows the penetration of the cells into a nanopore cavity for good adhesion, as illustrated in FIG. 1(c), where the arrows emphasize how cells, e.g., chondrocyte cells, can adhere and grow on the surface of these exemplary "open-topped" nanotubes, and how in some embodiment the surface of the array is coated with an extracellular matrix composition, e.g., collagen, proteoglycans or any mixture thereof.

In alternative embodiments, the desirable diameter range for nanotubes used in products of manufacture of this invention can be for the purpose of optimal cell adhesion and growth, while in alternative embodiments a desired height range can be for the purpose of minimizing the accumulated stress and delamination often associated with thick layer of $TiO_2$ or related nanotubes. Delamination can be a serious problem when nanotubes, e.g., when $TiO_2$ nanotube or $ZrO_2$ nanotubes, are more than a few micrometer thick; thus, in alternative embodiments, thinner layer nanotubes (e.g., $TiO_2$ nanotube or $ZrO_2$ nanotubes) are used to practice this invention.

In alternative embodiments, nanotubes used to practice this invention have a diameter dimension in the range of between about 30 to 600 nm outside diameter, or between about 50 to 400 nm diameter, or between about 70 to 200 nm diameter, and/or can have a height dimension in the range of between about 30 to 10,000 nm, and/or can have a thickness of between about 200 to 2,000 nm thickness, or between about 200 to 500 nm thickness. In alternative embodiments, longer and/or thicker nanotubes are used to practice this invention; however, in some embodiments, to give more room to store biological or other agents in a "nanodepot" (depending on the intended use of the product of manufacture of the invention), thick layer nanotubes, e.g., for implants, are less desirable.

Figure 2:
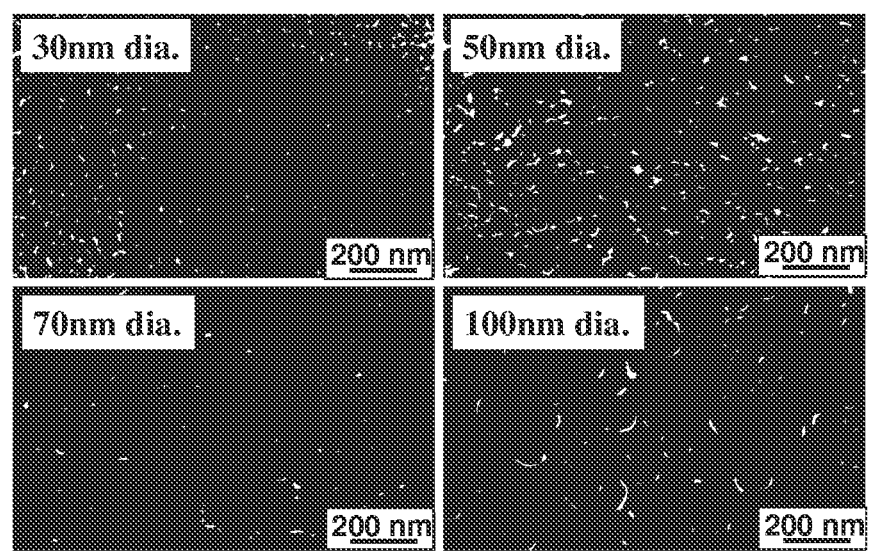
FIG. 2's four panels (at 30, 50, 70 and 100 nm diameter as indicated) illustrate SEM micrographs of exemplary self-aligned $TiO_2$ nanotubes with different diameters; scale bars are 200 nm; as described in detail, below.
Figure 3:
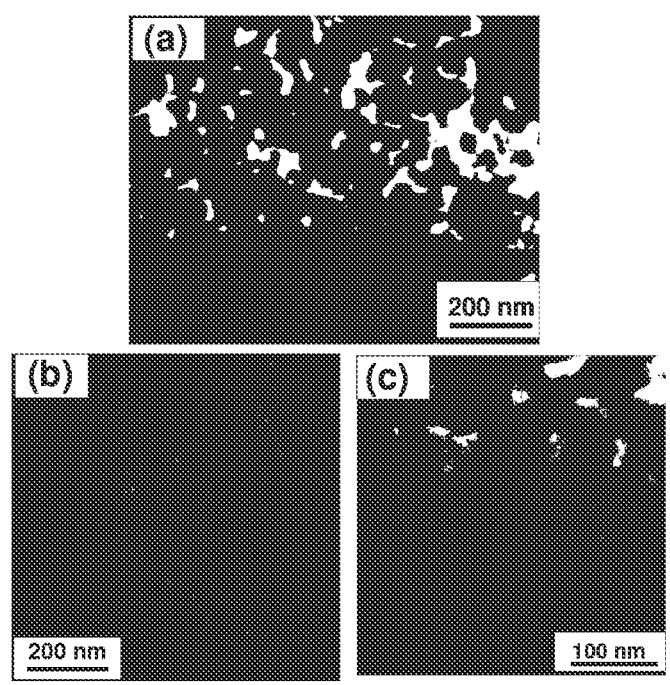
FIG. 3 illustrates structure of exemplary vertically aligned $TiO_2$ nanotubes on a titanium substrate, FIG. 3 (a) illustrates a scanning electron microscope (SEM) micrograph image at 200 nm, FIG. 3 (b) illustrates a longitudinal view transmission electron microscope (TEM) micrograph at 200 nm, FIG. 3 (c) illustrates a cross-sectional TEM at 100 nm; as described in detail, below.

In some embodiments, structures of the invention allow cells to adhere well to a surface to stay healthy and grow fast (e.g., by coating with an extracellular matrix composition, e.g., collagen, proteoglycans or any mixture thereof); the cells that may not adhere exhibit reduced or minimal growth. In the exemplary vertical nanotube structures of this invention, an examples of which are illustrated in FIG. 2 and FIG. 3, such an exemplary configuration is illustrated. This exemplary design of the invention allows desired accelerated chondrocyte growth and extracellular matrix formation. FIG. 2 and FIG. 3 illustrate scanning electron micrograph images (SEM micrographs) of self-aligned $TiO_2$ nanotubes with different diameters, the scale bars are 200 nm.

In alternative embodiments, titanium nanotubes are formed by electrolytic anodization, for example using 5% hydrofluoric acid and applying ~10-20 volts of potential, and allowing several minutes to a few hours depending on the temperature and other electrochemical process parameters. The resultant $TiO_2$ nanotube diameter is dependent on the anodization voltage. $TiO_2$ nanotubes can be prepared by various anodization processes: see e.g., Gong (2001) J. of Materials Res. 16(12):3331-3334; J. M. Macak (2005) Angew. Chem. Int. Ed., 44:7463-7465; Electrochimica Acta 50 (2005) 3679-3684 (2005) Angew. Chem. Int. Ed., Vol. 44, 2100-2102 (2005); Ghicov (2005) Electrochemistry Communications 7:505-509; Oh (2005) Biomaterials, Vol. 26, page 4938-4943; Oh (2006) Journal of Biomedical Materials Research, Vol. 78A, page 97-103; Oh (2009) Stem cell fate dictated solely by altered nanotube dimension, Proc. Natl. Acad. Sci. 106(7):2130-2135.

In alternative embodiments, titanium oxide nanotubes for biological applications of this invention significantly enhance bone growth; exemplary biological applications are described e.g., in the Oh et al. articles cited above.

In alternative embodiments, the structure of the anodized $TiO_2$ nanotube array, such as the diameter, spacing and height of nanotubes, is controllable during the electrochemical anodization process.

In alternative embodiments, the concentration of electrolytes is chosen, e.g., as described in articles by Gong, et al., Oh, et al, Macak, et al., and Ghicov, et al. cited above. Some exemplary electrolytes and their concentrations are; 0.5 wt % hydrofluoric acid (HF) in water, 0.5 wt. % ammonium fluoride ($NH_4F$) in 1 M ammonium sulphate (($NH_4$)$_2SO_4$), and 1 wt. % NaF in 1M $Na_2SO_4$ solution. In alternative embodiments, various anodization processing parameters such as the applied voltage, reaction time, the pH and the temperature of the bath, etc. are controlled and optimized as well.

In alternative embodiments, the base material can be pure Ti or can be an alloy based on Ti such as Ti—Al—V alloys or other solid solution hardened or precipitation hardened alloys with increased mechanical strength and durability. While accelerated chondrocyte growth and extracellular matrix formation illustrated herein are mostly using exemplary embodiments comprising substrate material of Ti and Ti oxide, in alternative embodiments, alloys used to make the products of manufacture of this invention can comprise other elements. Products of manufacture of this invention also can have Ti or Ti oxide by at least about 5%, 10%, 15%, 20%, 30%, 40%, 50%, 60%, 70%, 80%, 90% or more weight %. The use of other transition or refractory metals such as Zr, Hf, Nb, Ta, Mo, W, and their oxides, or alloys of these metals and oxides also can be used. Other materials such as stainless steels, Si, Si oxide, carbon, diamond, noble metals (such as Au, Ag, Pt and their alloys), polymer or plastic materials, or composite metals, ceramics or polymers, engineered into specific nanotube or nanopore array structure can also be utilized for products of manufacture, e.g., bio implants of this invention, and accelerated cell growth applications; and in alternative embodiments using a coating of Ti and Ti oxide, Zr, Hf, Nb, Ta, Mo, W and their oxides, and/or their alloys, with a thickness of at least about 1, 2, 3, 4, 5, 10, 15, 20, 30, 40, 50, 60, 70, 80, 90 or 100 or more nm and the coating coverage of at least about 5%, 10%, 15%, 20%, 30%, 40%, 50%, 60%, 70%, 80%, 90% or more of the total surfaces.

In alternative embodiments, the chondrocyte growth enhancing nanotube or nanopillar configuration materials are in the form of thin coating of metals or alloys, and at least about 1, 2, 3, 4, 5, 10, 15, 20, 30, 40, 50, 60, 70, 80, 90 or 100 or more nm thick surface portion of which is converted into a vertically aligned and adhering nanotube or nanopillar array structure.

In alternative embodiments, for chondrocyte cell growth and formation of extracellular matrix, compositions of the invention are designed to allow a continuous supply of nutrients including proteins, mineral ions, fluid, etc. is supplied to the cell through the flow of body fluids. For example, the gap (spacing) between adjacent $TiO_2$ nanotubules in the exemplary compositions of the invention as illustrated in FIGS. 1 to 3, serves the function of allowing the body fluid to continuously pass through and supply nutrients to a surface or side of a product of manufacture facing or adjacent to growing cells (e.g., supply nutrients to an opposing or "bottom" side of a product of manufacture facing growing cells). Exemplary gaps between the nanotubules are in the range of about between about 2 to 100 nm, or between about 5 to 30 nm Transmission electron microscope (TEM) photographs shown for an exemplary $TiO_2$ nanotubule array structure of the invention is illustrated in FIGS. 3(b) and (c), to give an average of approximately 15 nm spacing between the nanotubes.

Figure 4:
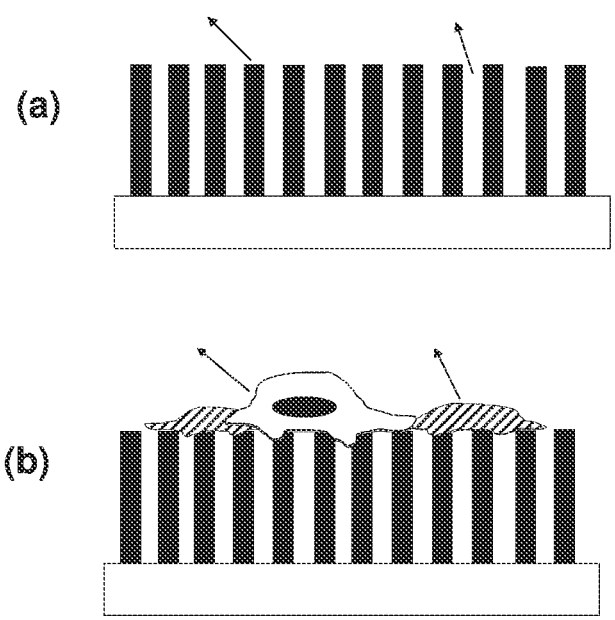
FIG. 4(a) and FIG. 4(b) schematically illustrate exemplary devices comprising nano-pillar configured $TiO_2$ arrays formed on titanium substrate to accelerate cell, e.g., stem cell or chondrocyte, proliferation and cartilage formation; which also can include osteoblast cell proliferation and bone osseointegration; as described in detail, below.

Nanotube and nanopillar array configurations of the invention can allow a continuous supply of cell grow nutrients, e.g., an exemplary nanopillar array configuration of the invention is illustrated in FIG. 4(a) and FIG. 4(b) can continuously supply of cell grow nutrients, and its nano topography structure and the gap between the nanopillars allows strong cell adhesion. The arrows in FIG. 4(a) emphasize the vertically aligned pillar array of $TiO_2$ "nanopillars", and that the spacing between the nanopillars allow for fluid flow. The arrows in FIG. 4(b) emphasize how cell, e.g., chondrocyte or stem cells, can adhere and grow in the nanopillars, and how an extracellular matrix (comprising e.g., collagen, proteoglycans, and the like) can be constructed as a layer on the nanopillar surface. This exemplary nanopillar structure, which cannot be produced by anodization technique utilized for fabricating the structures of FIGS. 1 to 3, can be formed on the surface of Ti, Zr, Hf, Nb, Ta, Mo, W, and/or their alloys, and/or a thin coating of these metals and alloys, e.g., by patterned masking and etching, or a combination of initial patterned etching and subsequent anodization.

Figure 5:
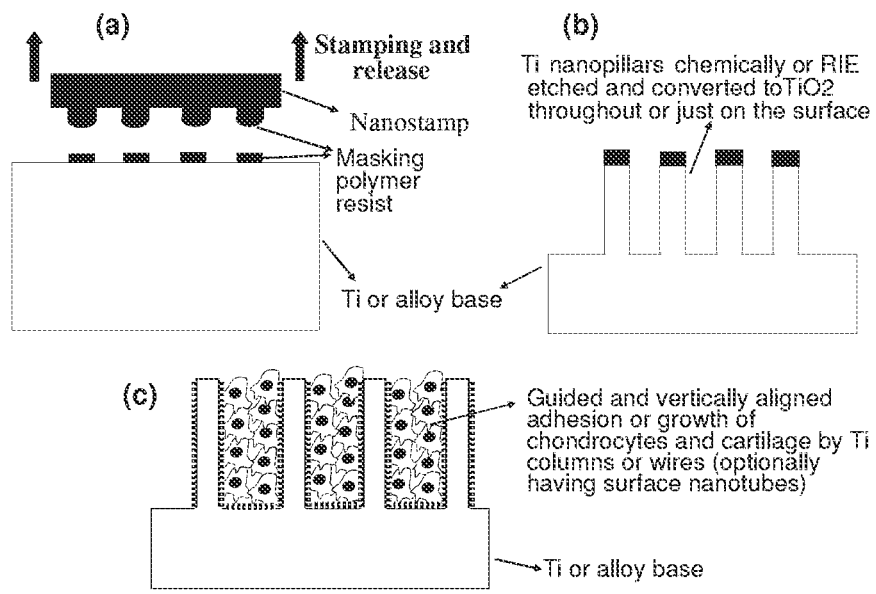
FIG. 5 illustrates an exemplary nano-imprint stamping process to fabricate a nanopillar array of Ti oxide or related metal and alloy oxide nanotubes.
Figure 6:
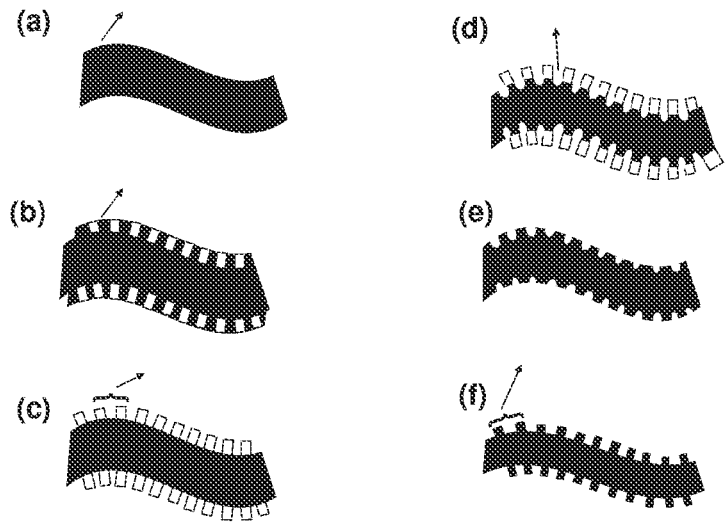
FIG. 6(a) to (f) illustrates an exemplary method for fabricating nanopillar or nanotube array on implant surface by guided etching using a vertically two-phase decomposed coating; as described in detail, below.

One exemplary way of fabricating a chondrocyte-enhancing nanopillar structure of this invention is to utilize nanoimprint technology; e.g., as illustrated in FIG. 5: nano stamping of polymer mask resist such as PMMA (polymethyl-methacrylate) layer can be carried out on the desired surface, in this exemplary embodiment, as a Ti or related metal and alloy surface. The PMMA can be first spin-coated into a thin layer, e.g., 20 to 200 nm thick layer, then the nanostamp can be pressed onto this uncured PMMA layer to pick up the resist islands, which is then transferred and imprinted onto Ti or alloy surface to leave islands of PMMA mask, as illustrated in FIG. 5(a). The Ti or alloy base is then chemically etched or reactive ion etched (RIE) to form the desired $TiO_2$ nanopillar structure of FIG. 5(b). The pillars can be wholly $TiO_2$ or only the surface of the pillars can be converted to $TiO_2$ by oxidation heat treatment of anodization treatment. Alternatively, the nanostamps can be made of patterned Si, metal or elastomer (PDMS), with the mechanically compliant elastomeric stamp allowing more reliable transfer of the masking resist islands. Because of directional nature of the nanopillars, cells, e.g., chondrocyte or stem cells, can adhere to the side of the nanopillars and form a vertically aligned guided cartilage column, FIG. 5(c). Such a guided vertical growth of cartilage approximates the important natural tendency of initial stage of human cartilage formation having a vertical geometrical arrangement. The initial vertical alignment (called a Deep Zone) is followed by more random Middle Zone, then by more horizontal Superficial Zone structure. Such a zonal cartilage formation can be made as described by Kim T K, et al. Experimental model for cartilage tissue engineering to generate the zonal organization of articular cartilage. Osteoarthritis Cartilage 2003; 11(9):653-664; Sharma B, et al. Designing zonal organization into tissue-engineered cartilage. Tissue Eng 2007; 13(2):405-414; Woodfield T B, eta al. Design of porous scaffolds for cartilage tissue engineering using a three-dimensional fiber-deposition technique. Biomaterials 2004; 25(18):4149-4161.

An alternative processing route to utilize nano-imprinting technology for formation of nanopillar or micropillar arrays as illustrated in FIG. 5(b) on Ti and related implant metals and alloys is to stamp a height-varying nanopattern of pillar or pore geometry into a thermoplastic or UV-curable polymer resist layer, with optional metal mask layer deposition and lift-off process, followed by vertical reactive ion etch to enable a pattern transfer to the underlying substrate.

Yet another exemplary technique of forming a location-guided and diameter-guided uniform nanopillar array of the invention, which in some embodiments is advantageous for fabricating exemplary nanopillar structures on non-flat surface of Ti or related metals and alloys, is to introduce guided etching using a vertically two-phase decomposable coating as illustrated in FIG. 6(a) to (f). In this exemplary technique: first, Ti implant or substrate for chondrocyte culture and cartilage growth is coated with a material which is then decomposed into a vertically aligned two-phase structure. An example of such a decomposable material is a diblock copolymer layer which, on heating, can decompose into vertically aligned two phases. See e.g., M. Park et al., "Block copolymer lithography: Periodic arrays of $10^{11}$ holes in 1 square centimeter", Science, Vol. 272, page 1401 (1997).

Another exemplary composition of the invention comprises decomposable material leading to a vertically aligned two-phase structure, such as a spinodally decomposing alloy, e.g., as described by N. Yasui et al, "Perpendicular recording media using phase-separated AlSi films", Journal of Applied Physics, Vol. 97, page $10N_{103}$ (2005). Either during the thin film deposition with self-heating during the RF plasma sputter deposition process or with post-deposition annealing ~100-700° C., a desirable vertically aligned nano pore structure or nano island structure can be obtained from a spinodal alloys in general. In the case of Al—Si alloy films, with proper chemical etching, Al can be selectively etched while Si oxidizes into $SiO_2$ porous membrane or $SiO_2$ island array, thus creating a nanopore or nanopillar structure depending on the relative volume fraction of the two phases.

Yet another exemplary composition of the invention comprises decomposable material leading to a vertically aligned two-phase structure, is the employment of anodized aluminum oxide (AAO) structure, for example, described by A. I. Gapin et al, J. Appl. Phys. 99, 08G902 (2006). The nanopore arrays can be used as a mask to chemically etch the substrate rods or wires (such as made of Ti, Zr, Hf, Nb, Ta, Mo, W metals and related alloys) to form nanopillars or nanopores.

In one embodiment, after an exemplary decomposable coating is added and made to decompose into aligned two phase structure, as illustrated in FIG. 6(b), one of the phases is removed from the two phase structure via differential etching, e.g., by chemical etching or ion etching to exhibit a nano island array FIG. 6(c). FIG. 6(c) illustrates a nano-island coating left after preferential etching away of one of the two phases. The coating of textured material can be a co-sputtered layer, a decomposable diblock co-polymer, a spinodally decomposing alloy, and the like. Etching of Ti or alloy base through the masking islands can produce the exemplary nanopillar array of FIG. 6(d). After the coating material is removed, as illustrated in FIG. 6(e), optional additional etching or guided anodization process may be utilized to further increase the depth of the nanopillars, as illustrated in FIG. 6(f). FIG. 6(f) illustrates the optional additional etching or anodization to produce a "deeper" or higher nanopillar or nanotube, which can act as an implant surface.

In one embodiment, products of manufacture of the invention comprise diblock copolymers, which can comprise two chemically different polymer chains or blocks while they are joined by a covalent bond. Because of this connectivity constraint yet chemical incompatibility with each other, the diblock copolymers tend to phase separate and self assemble into an ordered (often with a hexagonal geometry), nanoscale, mixed-phase composites. Depending on the chemistry and decomposition conditions, they can form an ordered array with one of the polymer components taking a nano-cylinder shape embedded in the other polymer component. Examples of diblock copolymers used in products of manufacture of the invention include a mixture of polystyrene-polybutadiene and that of polystyrene-polyisoprene. The diblock copolymers can be diluted with a solvent such as toluene, and can be dip coated, brush coated or spray coated on a substrate. When the heat is applied and drying proceeds and the copolymer concentration and temperature reaches a critical point, the phase decomposition of the diblock copolymer into an ordered structure takes place. The desired temperature rise to nucleate and grow the ordered decomposed diblock copolymer structure can be between about range of between about 50° C. to 350° C., or between about 100° C. to 250° C.

The spinodal alloys can be spontaneously decomposed into a uniform two phase structure by heating to a high temperature within the spinodal phase stability range. Fe—Cr—Co, Al—Ni—Co—Fe, Cu—Ni—Fe, Cu—Ni—Co, and Al—Si alloys are well known examples of spinodally decomposing alloys. Due to the difference in chemical etchability between the two decomposed phases, a nano-island mask structure, e.g., as illustrated in FIG. 6(c) can be obtained over a large area.

Another embodiment of the present invention uses nano-depot spaces within nanotubes or in the space between nano-pillars; these structures can be utilized to conveniently store drugs and/or biological agents desirable for enhanced culture of chondrocytes, like a growth factor, other biomolecules, antibiotics, etc. which can be slowly released from the nano-depot, which can be a $TiO_2$ nanotube surface layer. In alternative embodiments, the nanoscale space of the $TiO_2$ nanotubes or spacing between the nano-pillars, as compared to microsized pores, has an advantage of being able to keep the stored drugs and/or biological agents much longer and allow slower release over a longer period of time. Controlled slow release of drugs and/or biological agents such as growth factors, antibiotics, such as penicillin, streptomycin, vancomycin, hormones and the like, can be incorporated; e.g., antibiotics can prevent infections near the chondrocyte-related implant. Growth factors and/or drugs, etc. stored and slowly released from the nano-depot space can also enhance cell growth and/or differentiation, e.g., enhance chondrocyte, stem cell, totipotent cell, multipotent progenitor cell and/or pluripotent cell formation and/or differentiation over extended period of time.

In alternative embodiments of the invention, the drugs and/or biological agents that are stored in nano-depot spaces (e.g., within nanotubes or in the space between nano-pillars) include growth factors, collagens, various proteins/biomolecules, genes, DNAs, antibiotics, hormones, therapeutical drugs, and/or functional particles like magnetic, metallic, ceramic, polymer particles. In alternative embodiments, biological agents can comprise a fibroblast growth factor (FGF), an epidermal growth factor (EGF), a vascular endothelial growth factor (VEGF), a transforming growth factor beta-1 (TGF-β1) or a transforming growth factor beta-2 (TGF-β2), a bone morphogenic protein (BMP) (e.g., an agent that stimulates chondrocyte growth, maintenance and/or differentiation), fibroblast growth factors and/or vascular endothelial growth factors. In alternative embodiments, a biological agent is or comprises an isolated protein, an autologous protein, and/or a recombinantly generated polypeptide.

The functional particles can be made of magnetic oxide particles or metallic particles, and can be utilized for remotely actuated RF heating and creation of temperature gradient for accelerated or switch-on, switch-off release of the drugs and/or biological agents stored in the nano-depots, e.g., within nanotubes or in the space between nano-pillars.

Figure 13:
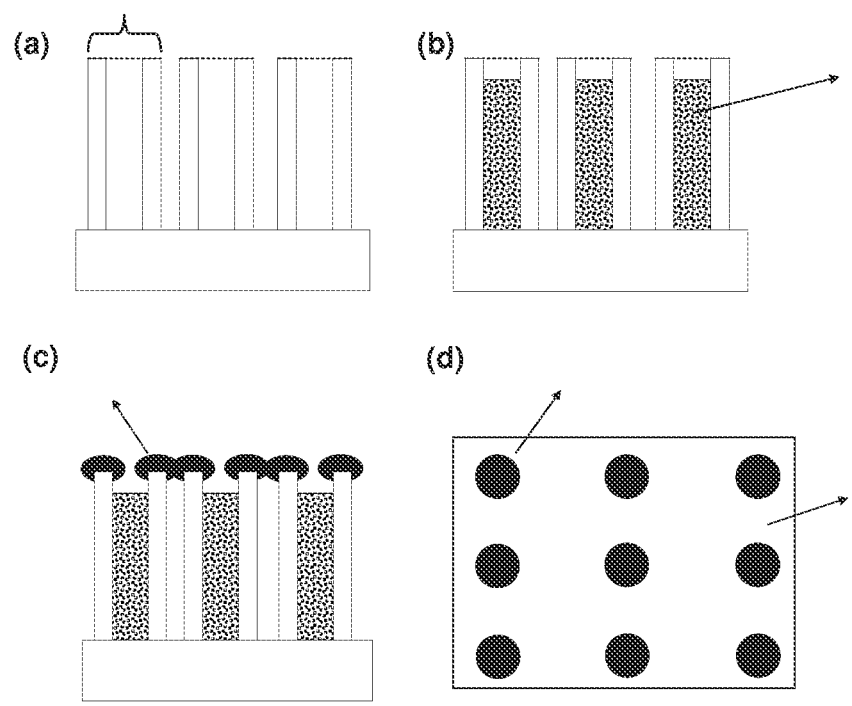
FIG. 13 schematically illustrates an embodiment of $TiO_2$ nanotube based implants comprising nanotubes with slow-releasing drugs and/or biological agents stored in the vertically aligned nanotube pores.

Referring to the drawings, FIG. 13 schematically illustrates an alternative embodiment of the invention comprising $TiO_2$ nanotube based implants comprising nanotubes with slow-releasing drugs and/or biological agents stored in the vertically aligned nanotube pores: FIG. 13 (*a*) As-made $TiO_2$ nanotubes, FIG. 13 (*b*) Drugs and/or Biological agents stored in the nano-depots, FIG. 13 (*c*) Diameter reduced nano-depot entrance for slower release of stored drugs and/or biological agents.

Figure 23:
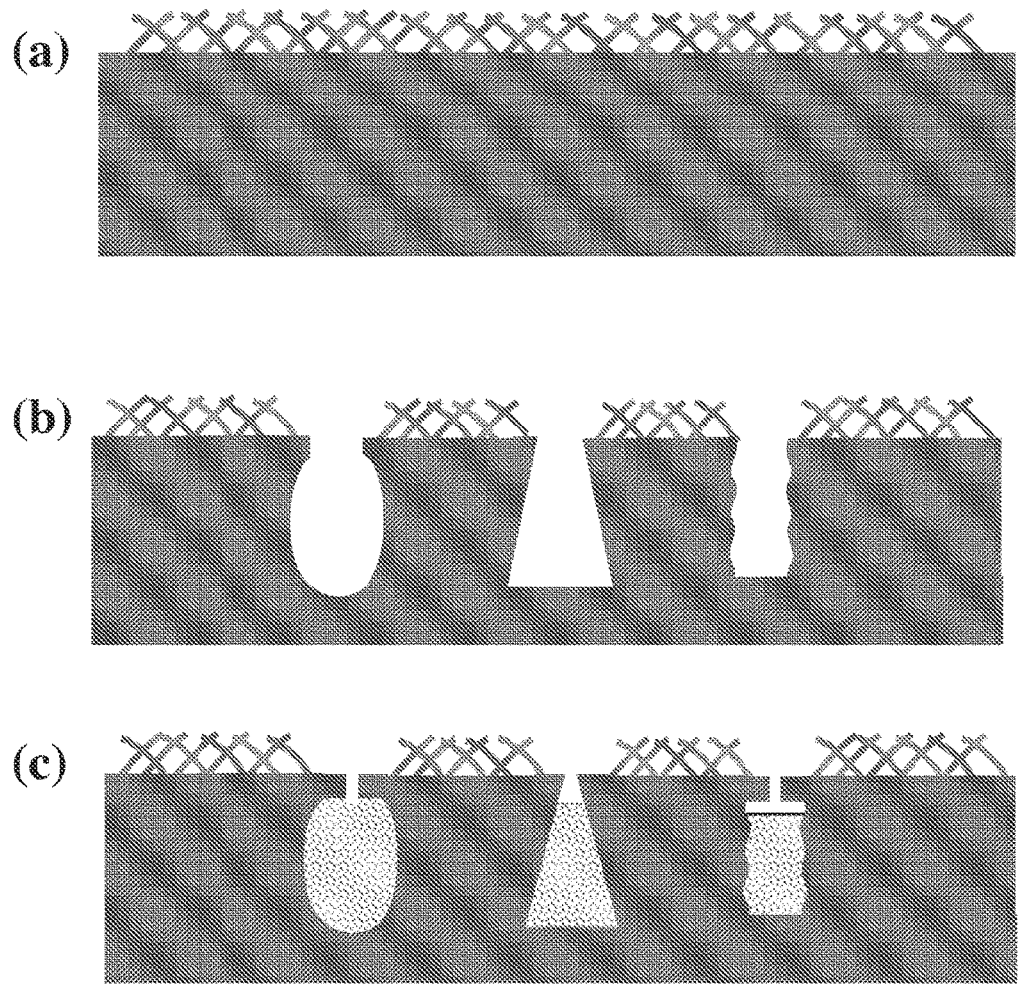
FIG. 23(a), FIG. 23(b) and FIG. 23(c) illustrate embodiments of the invention comprising exemplary flat or dual-structured Ti implants having compliant, three-dimensional wire assembly structure; as described in detail, below.
Figure 24:
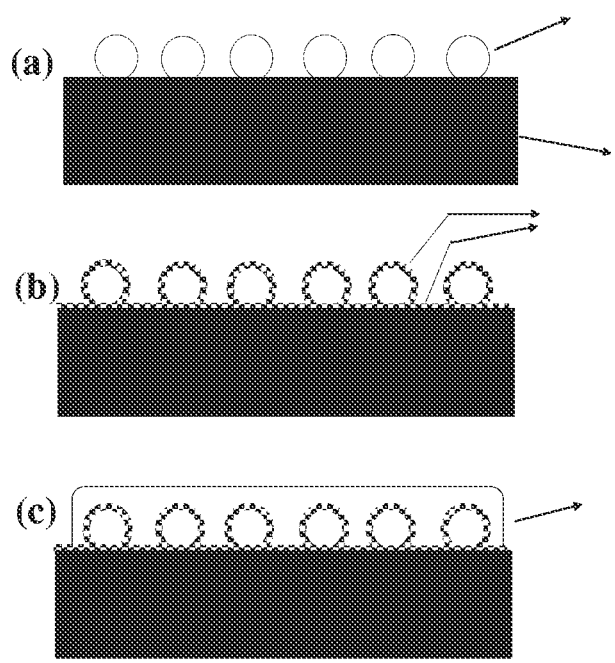
FIG. 24(a), FIG. 24(b) and FIG. 24(c) illustrate embodiments of the invention comprising exemplary $TiO_2$ compositions of the invention comprising Ti or Ti alloy particles or fibers; as described in detail, below.

For the purpose of storing more drugs and biological agents in the nanodepot, the $TiO_2$ nanotubes can be made taller, e.g., nanotubes between about 1 to 50 micrometers tall, or alternatively nanotubes between about 1 to 10 micrometers tall. However, taller or thicker nanotube layer tends to introduce accumulated stresses and make the layer susceptible to delaminations. From this point of view, shorter nanotubes between about 200 to 500 nm tall, or about 20, 30, 40, 50, 60, 70, 80, 90, 100, 125, 150, 175, 200, 225 or 250 or more nm in height may be preferred, depending on its use and/or method of manufacture. The balance between the desire to store more biological agents and the need to keep the nanotube height short may have to be carefully weighed depending on each specific application. An alternative embodiment comprises taking a duplex depth structures as illustrated in FIG. 23, in which a microcavity is utilized to store a larger amount of biological agents, stem cells, drugs, and chemicals while the nanotube height is maintained short on the implant surface and associated spingy wire surface.

An alternative embodiment comprises slowing down the release of the stored drugs and/or biological agents by making the nanotube entrance narrower by intentional sputtering or evaporation deposition of $TiO_2$ or Ti metal (to be oxidized later by either anodization or by low temperature heat treatment in air or oxygen-containing atmosphere). This is schematically illustrated in FIG. 13(*c*). While regular vertical incident deposition also tends to form such bottle necks, an optional oblique incident deposition with rotating substrate during deposition makes it easier to form the intentional bottle neck configuration.

In an alternative embodiment, diameter reduction is by bottleneck addition, such as by sputter deposition of Ti, $TiO_2$, or other metals, alloys, oxides or polymers, can be conducted to a diameter of less than 20 nm, or alternatively less than 10 nm near the entrance to the pores to minimize unwanted release of liquid agents such as dissolved antibiotics, small molecule chemical growth factors, DNAs and genes. For larger molecule biological agents such as proteins and polymers, the bottle neck diameter has to be adjusted accordingly, e.g., approximately 40 nm diameter bottleneck to allow the release of some of these larger diameter molecules from the nanotube nanodepot space.

In alternative embodiments, a $TiO_2$ nanotube structure having the appropriate diameter may be essential for enhanced cell growth, e.g., at least 50 nm diameter, for osteoblast and chondrocyte cells. This objective may conflict with the exemplary nanodepot embodiment comprising intentionally introducing the bottleneck configuration at the top entrance to the nanotube pores and the in-between gap regions so that the biological agents, e.g., liquid-based chemicals and/or drugs, do not get released too rapidly. In order to resolve these conflicting requirements, alternative embodiments comprise a duplex distribution of the nanostructure dimensions such that the nano-depot regions having intentionally bottle-necked pore structure are mixed and distributed together with regular nanotube regions which do not have the bottleneck diameter reduction. This exemplary embodiment is schematically illustrated in FIG. 13(*d*). The former will serve as a storage and slow release of biological agents while the latter will serve to enhance cell adhesion and growth.

The average area of each of the distributed nano-depot regions for drug- or biological agent release can be adjusted as needed, for example in the range of 1 μm-1,000 μm. Each of these regions contains many nanodepot reservoirs, and can have circular, rectangular, or irregular shape. The distribution of these regions on the implant surface can be periodic or random. In alternative embodiments, the relative area fraction of the drug release regions can be in the range of between about 2% to 50%, or between about 10% to 30%, of the total available surface area for cartilage or bone growth depending on the specific needs.

Figure 14:
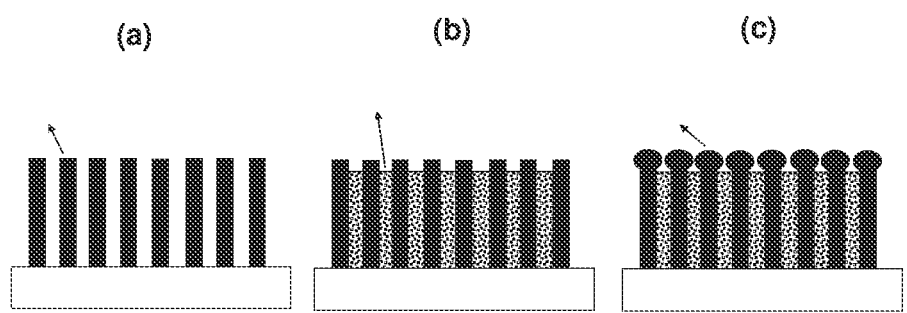
FIG. 14 schematically illustrates an embodiment of $TiO_2$ nano-pillar configured implants comprising slow-releasing drugs and/or biological agents stored in the gap between vertically aligned nanopillars.

A similar nano-depot storage and slow release of the drugs and/or biological agents as in the case nanotube array structure of FIG. 13 can also be accomplished with the nano-pillar array structure, according to the invention. This is schematically illustrated in FIG. 14. With the intentionally induced bottleneck configuration, the slow rate release is achieved.

In one embodiment of the invention, the methods of the invention utilize vertically aligned $TiO_2$ or Ti metal and/or related materials in nanotube or nano-pillar array configurations; and in one aspect incorporating nano-depot based reservoirs for the slow release of drugs and/or biological agents. These configurations can substantially enhance the kinetics and quantity of chondrocyte functionality and extracellular matrix formation, as well as cartilage growth rate, by e.g., at least about 1%, 2%, 3%, 4%, 5%, 10%, 20%, 30%, 40%, 50%, 60%, 70%, 80% or 90% or more, as compared with the same bio implant material or bio substrate material without these nanotube or nanopillar structures of this invention.

In another embodiment of the invention, the products of manufacture and methods of the invention incorporate bonded macro or microscale scaffold structures comprising springy wires or mesh wires, for example as illustrated in FIGS. 17 to 23. The surfaces of these scaffold wires are also nanopatterned as nanotube or nanopore structures to enhance chondrocyte adhesion and growth. In alternative embodiments, "springy" and "compliant" are terms that are quantitatively defined, e.g., in some embodiments as "a coil-like or curved or bent metal wire array or forest in the metallic state that can be elastically compressed (e.g., before implanting), e.g., that can be elastically compressed by at least about 5%, 10%, 15%, 20% or 25% or more reduction in height, and in some embodiments upon releasing the applied load the original geometry is restored without noticeable permanent plastic deformation, e.g., less that about 10%, 9%, 8%, 7%, 6%, 5%, 4%, 3%, 2% or 1%, or less permanent compression left.

Figure 26:
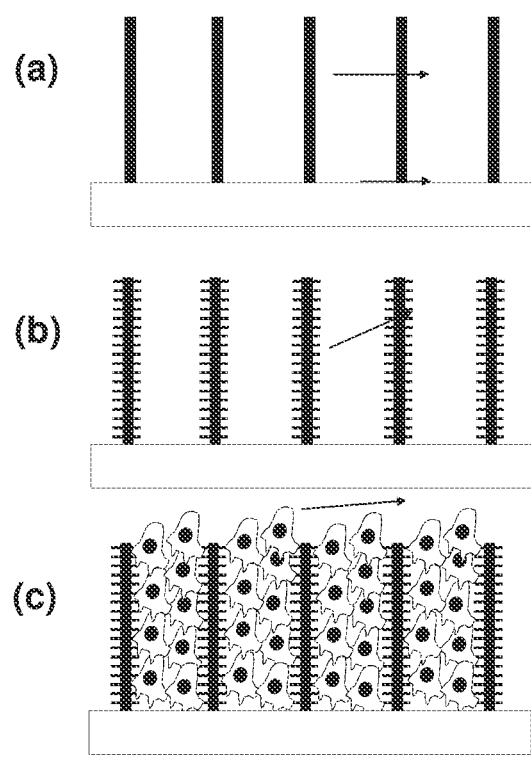
FIG. 26(a), FIG. 26(b) and FIG. 26(c) illustrate embodiments of the invention comprising exemplary compositions of the invention comprising Ti or Ti alloy wire or ribbon arrays unidirectionally or vertically aligned, with the surface of wires or ribbons anodized to form TiO2 nanotubes; in this exemplary embodiment the chondrocyte or cartilage growth is guided somewhat vertically along the Ti wire or ribbon direction, as described in detail, below.
Figure 27:
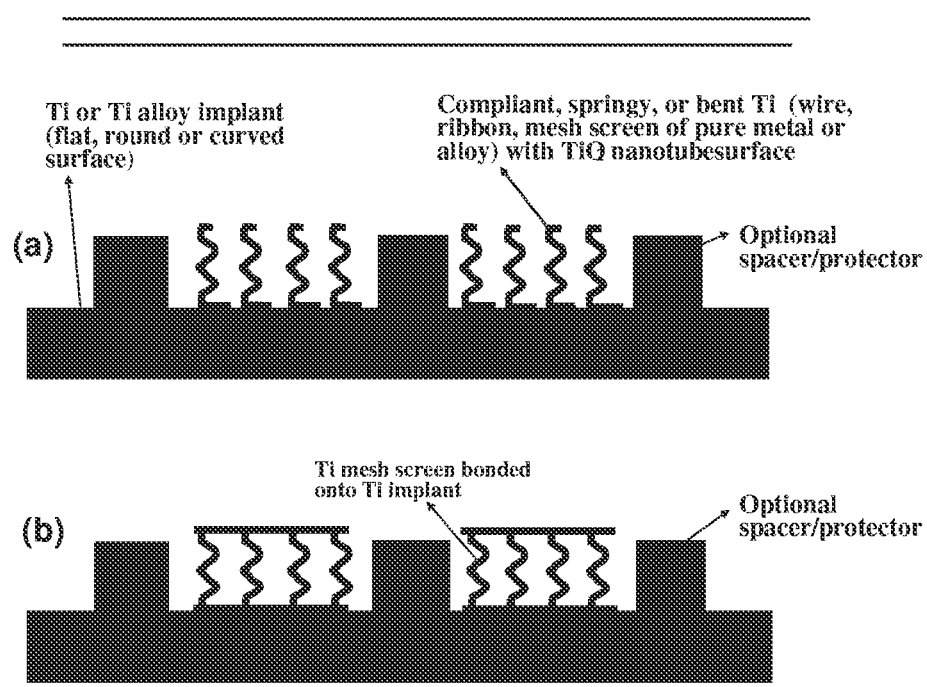
FIG. 27(a) and FIG. 27(b) illustrate embodiments comprising exemplary compositions of the invention comprising compliant, springy or bent Ti or Ti alloy wires, mesh screens or ribbon arrays, as described in detail, below.

Yet in another embodiment of the invention, the products of manufacture and methods of the invention utilize patterning and etching of the implant surface to introduce vertically aligned macro or micro pillars of Ti and related metals and alloys such as Ti—Al—V and Zr, Hf, Nb, Ta, Mo, W. An example structure is illustrated in FIG. 26. These metal pillars, according to the invention, are processed in such a way that the surfaces of each of these metal pillars are also nanopatterned to provide nanotube or nanopore structures for enhanced chondrocyte adhesion and growth. These vertical pillar metal scaffolds with chondrocyte adherent surfaces support a three-dimensional, vertical-direction-guided growth of chondrocytes and cartilages approximating the initial stage of natural cartilage growth in human.

Products of manufacture of this invention can be useful for a variety therapeutic applications for human and animals, including use for enhanced cartilage growth, initiation of cartilage growth and/or cartilage repair. The compositions and methods or the invention provide supportive scaffolding for new cartilage growth, enhanced cartilage growth, initiation of cartilage growth and/or cartilage repair at any moveable, cartilaginous, and synovial joint site including but not limited to: Intervertebral discs (or intervertebral fibrocartilage), bronchial tubes, Thumb and fingers (between the metacarpal and carpals); Wrist; Elbow (between the humerus and the ulna and between the radius and the ulna); Shoulder; Hip; Knee; Ankles; Feet and toes (between tarsals and metatarsals); Intervertebral discs of the spinal cord; Rib cage and/or ears or noses, e.g., for reconstructive or plastic surgery purposes. The compositions and methods of the invention provide supportive scaffolding for new cartilage growth, enhanced cartilage growth, initiation of cartilage growth and/or cartilage repair for any cartilaginous tissue, including elastic cartilage, hyaline cartilage and fibrocartilage. Products of manufacture of this invention can be useful new cartilage growth, enhanced cartilage growth, initiation of cartilage growth and/or cartilage repair for endochondral ossification, osteoid and/or periosteum formation and calcification, as some forms of bone formation require a pre-existing cartilage structure.

The compositions and methods of the invention enable joint movement while providing the structural support and chemical environment for new or repaired cartilage tissue to grow, e.g., to fill defects or injuries, e.g., to replace damaged, infected, aged, or diseased cartilage caused by various diseases such as: Arthritis; Osteoarthritis (e.g., due to sports injuries, extreme trauma, impact injury, or repeated micro trauma); Isolated femoropatellar osteoarthritis (e.g., kneecap osteoarthritis); Rheumatoid arthritis (a chronic, systemic autoimmune disorder that causes the immune system to attack the joints) lupus or any other autoimmune disease where the immune system attacks directly or indirectly the body's cells and tissue resulting in inflammation and tissue damage, particularly in osteonecrosis of the joint; Septic arthritis caused by joint infection; a previously infected or injured knee or other joint.

Figure 15:
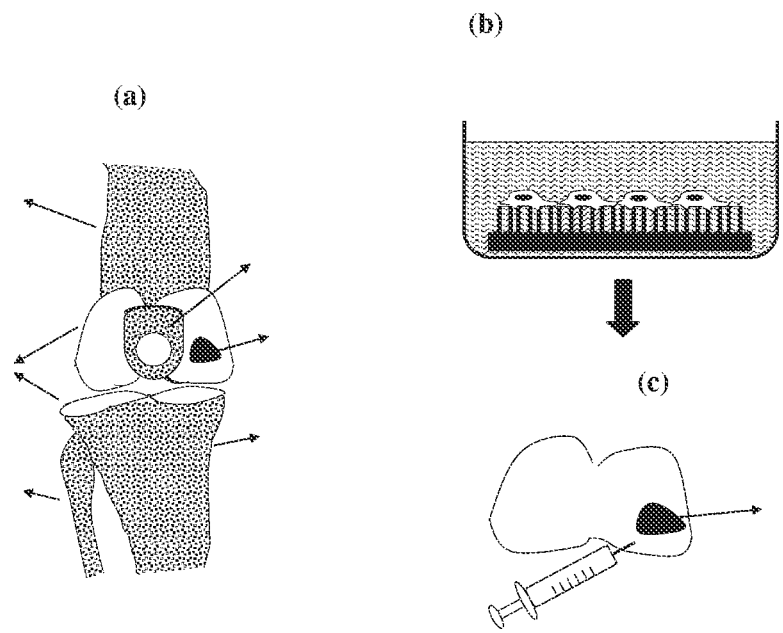
FIG. 15 schematically illustrates.
Figure 16:
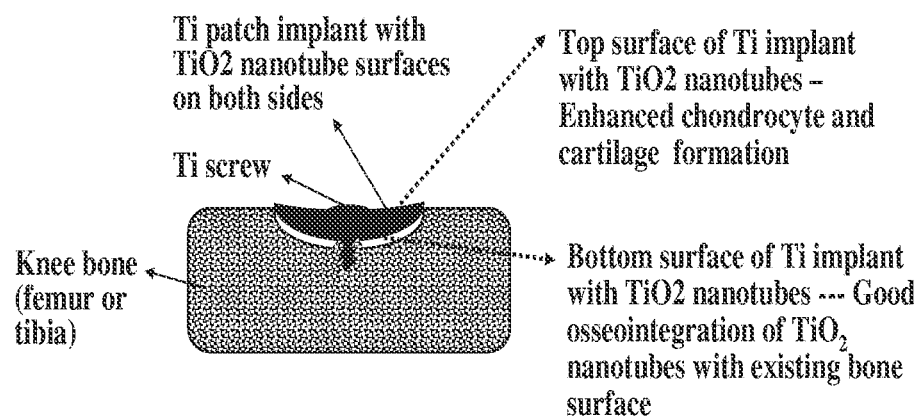
FIG. 16 schematically illustrates an embodiment of the invention comprising a Ti patch implant with $TiO_2$ nanotubes on two surfaces, e.g., a "top" surface for chondrocyte growth and an opposing (e.g., bottom) surface for strong osseointegration with existing bone surface, and enhanced chondrocyte and cartilage formation on the top surface; as described in detail, below.

At least two different embodiments of the inventions are described in FIG. 15 and FIG. 16. One embodiment to repair damaged cartilage, for example to repair and restore an articular cartilage defect illustrated in FIG. 15(a), is to utilizes the chondrocyte enhancing characteristics of the $TiO_2$ nanotubes or nanopillars and prepare in-vitro culture of patient's own chondrocytes, FIG. 15(b), which is then injection transplanted into the cartilage defect regions in human or animal body, FIG. 15(c).

Another embodiment is to utilize $TiO_2$ nanotube or nanopillar material as a surface coating implant material on a patch bone implant Ti piece to be inserted into the area of cartilage defect, as illustrated in FIG. 16.

An exemplary process steps are as follows.
  i) The defective or injured area of cartilage, see an example shown in FIG. 15(a), is first cleaned by removing the damaged tissues.
  ii) An appropriately shaped Ti implant piece is fabricated by machining, casting, stamping, or other means so that a desirable shape resembling the removed tissue and bone area as illustrated in FIG. 16. The Ti patch implant material is processed (e.g., as described herein) by e.g. anodization or nano-mask pattered etching, or combination of these two process approaches, to possess the $TiO_2$ nanotube or nanopillar structure on both top and bottom (or opposing) surfaces (more generally speaking, on all outside surfaces of the Ti implants). As illustrated in FIG. 16, the top surface of the $TiO_2$ nanotubes of the top surface of the implant act to enhance cell, e.g., stem cell or chondrocyte, growth and subsequent cartilage formation; the bottom (or opposing) surface of the implant, also having $TiO_2$ nanotubes, facilitates osseointegration of the implant with existing bone.
  iii) The patch implant Ti (or a total joint replacement Ti if needed) is then placed on the existing bone and fixed in position by using one or more Ti or stainless screws, which can be left permanently even after osseointegration of the Ti implant with the existing bone, FIG. 16. Alternatively, a temporary fixture consisting of removable or biodegradable strings or straps can be used until the natural osseointegration at the bottom (or opposing) side is essentially completed.

In alternative embodiments, the cartilage growth structures are not limited to planar material configurations, but also comprise additional variations and embodiments, including comprising a $TiO_2$ nanotube surface on a compliant 3-D substrate, e.g., as illustrated in FIGS. 16 to 29. Other exemplary scaffold structures, such as vertically aligned Ti metal pillar arrays or nanoparticle arrays, used to practice this invention are also described in these figures.

In one aspect, an advantage of nanotube or nanopillar configurations of this invention is that a strong osseointegration of the implant with the existing bone occurs at the bottom (or opposing) surface (at the interface between the implant and the bone facing it), while a much enhanced chondrocyte growth and cartilage formation occurs at the top surface of the implant.

Alternative embodiments of the invention comprise (e.g., incorporate) stem cells, e.g., a mesenchymal stem cell, an adult stem cell, an induced pluripotent stem cell (abbreviated as iPS cell or iPSC) and/or an embryonic stem cell, a human mesenchymal stem cell or human embryonic stem cell, or an artificially created stem cells through gene modification of somatic cells. In one embodiment, when stem cells such as human mesenchymal stem cells (hMSCs) are cultured without chondrogenic inducing media, the $TiO_2$ type nanotube, nanowire and/or nanopore and related nanostructures, according to the invention, upregulate differentiation into chondrocytes over cultures by nanotopography alone. While the invention is not limited by any particular mechanism of action, such a behavior is related to the recently discovered phenomenon on the effect of nanotubes causing enhanced and preferential hMSC differentiation to osteoblast cells by nanotopography structure alone even in the absence of differentiation-inducing agents; as described e.g., by Oh (2009) Stem cell fate dictated solely by altered nanotube dimension, Proc. Natl. Acad. Sci. USA 106(7): 2130-2135; also cited above.

In one embodiment, when stem cells such as human mesenchymal stem cells (hMSCs) are cultured with chondrogenic inducing media, the $TiO_2$ type nanotube, nanopore and related nanostructures, according to the invention, upregulate differentiation into chondrocytes over cultures with the aid of the nanotopography of the products of manufacture of this invention. Exemplary chondrogenic inducing media comprise a chemically defined medium comprising, for example, serum-free DMEM, ascorbate, dexamethasone, L-proline, sodium pyruvate, ITS-plus, antibiotics, and recombinant human transforming growth factor-β1 (TGF-β1).

Stem cells cultured in the chondrogenic media on nanotube, nanowire and/or nanopillar-comprising products of manufacture of this invention proliferate and differentiate into the chondrogenic lineage as the stem cell differentiation; which in some embodiments is influenced by both the cell-substrate interactions from the topographical cues of the surface in addition to the chemical cues of the inducing media. In some embodiments, nanotopography of nanotube, nanowire and/or nanopillar surfaces of nanotube, nanowire and/or nanopillar-comprising products of manufacture of this invention thus play an essential role in mimicking the cell and extracellular matrix (ECM) organization that is found, for example, in the natural cartilage zone, that would play a role in directing MSC differentiation into chondrocytes. By combining synthetic $TiO_2$ nanostructures having topographical cues combined with the biochemical cues (e.g., TGF-β1 and/or BMPs), the products and methods of the invention further enhance chondrocyte growth and/or differentiation to chondrocytes from progenitor cells (e.g., stem cells), and in alternative embodiments the products and methods of the invention enhance the upregulation of chondrogenic maker expressions (genes, proteins, ECM, etc.) in colony-forming unit-fibroblast (CFU-F), marrow stromal cell or mesenchymal stem cell (MSC), stem cell, totipotent cell, multipotent progenitor cell and/or a pluripotent cell cultures.

Figure 29:
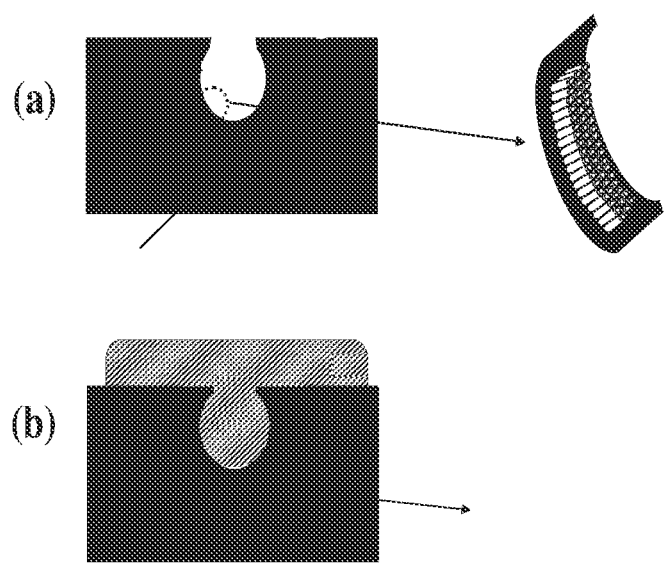
FIG. 29(a) and FIG. 29(b) illustrate embodiments of the invention comprising exemplary compositions comprising nanotubes and/or nanopores on non-Ti surfaces such as ceramics, polymers, plastics and other non-Ti metals (e.g., Si, Au, Pt, Al) deposited or made by e.g., anodization, as described in detail, below.

In alternative embodiments, the nanotube, nanopillar and/or nanoribbon scaffolds (comprising e.g., a metal or a metal oxide such as Ti or $TiO_2$), and/or microcavities or macrocavities, are configured so as to store and release chemicals, drugs and/or biological agents, e.g., growth factors, e.g., chondrogenic growth factors such as FGF, EGF, BMPs and/or TGF-β1 and the like, in a well-controlled fashion. The chemicals, drugs or biological agents, e.g., growth factors, can be stored either in nanodepot cavities of nanotubes or nanopillars, or between nanotube, nanopillar and/or nanoribbon scaffolds, as illustrated for example in FIGS. 6, 13, 14, 17, 18, 20, 21, 26, or microcavities or macro cavities such as shown in FIGS. 23 and 29.

While the naturally occurring stem cells in human or animal body contribute somewhat to the growth of bones and cartilages, in some embodiments this invention comprises use of stem cells and/or chondrogenic growth factors with products of manufacture of the invention to further accelerate the cartilage growth. In alternative embodiments, the stem cells themselves can be supplied either as a part of the cartilage growth media or can be stored and supplied from macro/micro cavities of products of manufacture of the invention, e.g., in the exemplary structures illustrated in FIGS. 23 and 29. In alternative embodiments, the nanodepot entrance to the nanopores or nanotubes on Ti implants or on scaffold wires is geometrically modified to have controlled diameter bottleneck structure first. In alternative embodiments, the nanodepot storage space is then loaded with drugs and/or growth factors such as FGF, EGF, BMPs and/or TGF-β1 and the like, and allowed to follow precisely planned release rate of the growth factor over desired period of time, e.g., from 1 day to more than 60 days, or more, according to the pre-designed pore entrance size of the nano-depots.

Figure 17:
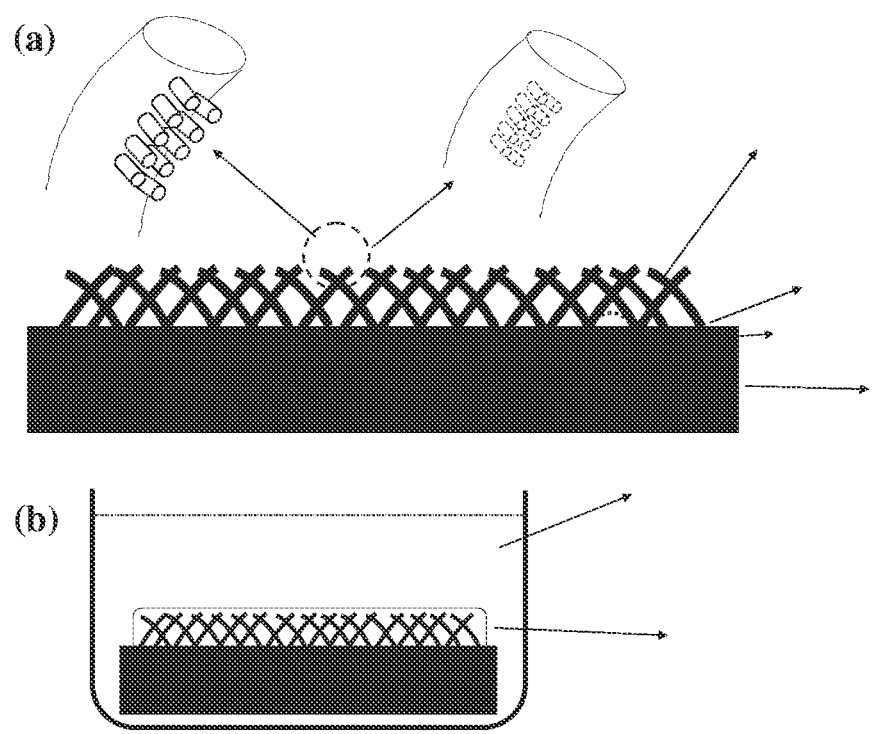
FIG. 17(a) illustrates an embodiment of the invention comprising a three-dimension Ti implant surface; extended and protruding wire-like biocompatible structures are shown.
FIG. 17(b) schematically illustrates three-dimensional and geometrically secured cartilage growth around compliant, hairy or spring-shaped Ti having TiO2 nanotubes or other nanostructures; as described in detail, below.
Figure 18:
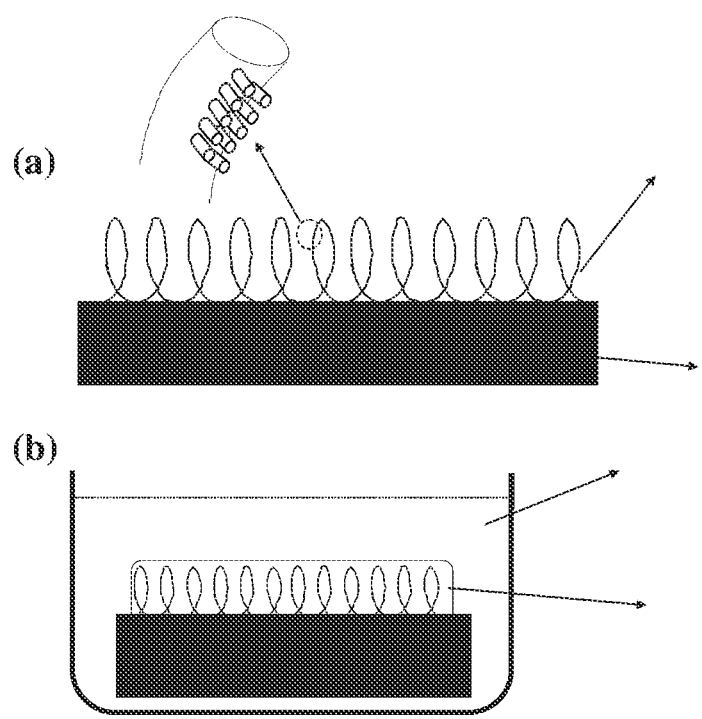
FIG. 18(a) illustrates an embodiment of the invention comprising exemplary $TiO_2$ nanotube or nanopore arrays; hairy-shaped or mesh-screen shaped surface structures.
FIG. 18(b) schematically illustrates an embodiment of three-dimensional and geometrically secured cartilage growth around compliant spring-shaped Ti wires having TiO2 nanotubes or other nanostructures; as described in detail, below.
Figure 19:
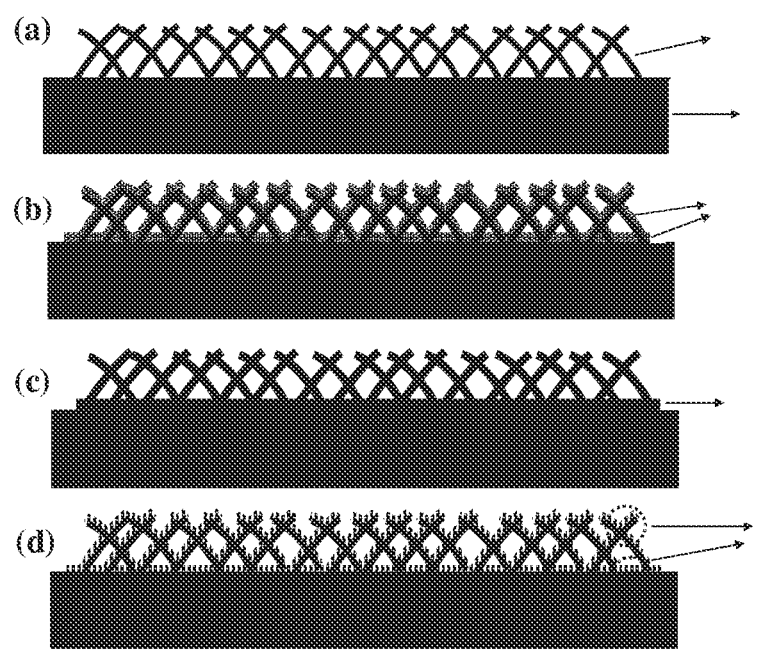
FIG. 19(a) to (d) illustrate an embodiment of the invention comprising diffusional bonding of Ti hairy-shaped or Ti mesh-screen shaped surface structures onto an exemplary composition of the invention, e.g., a Ti implant; as described in detail, below.
Figure 20:
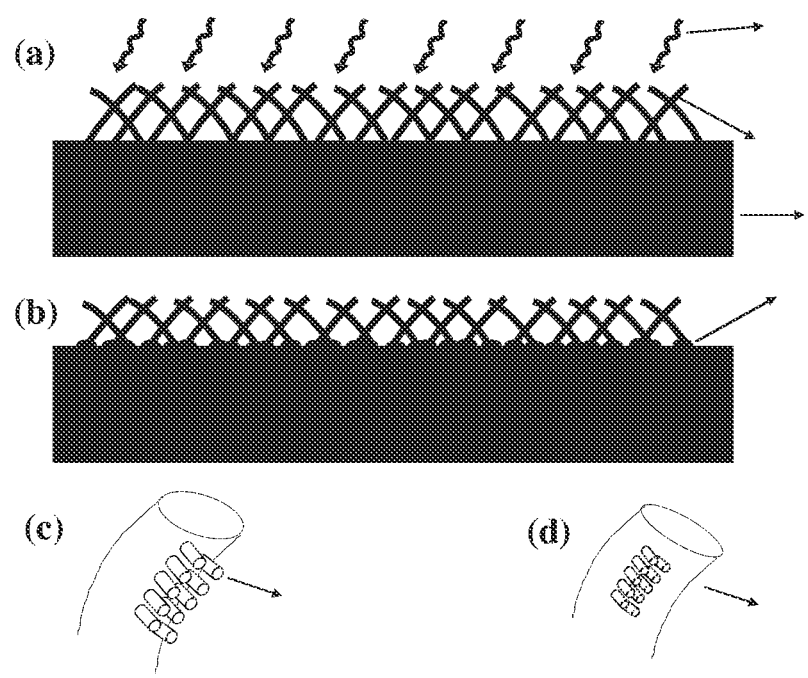
FIG. 20(a) to (d) illustrate an embodiment of the invention comprising melt-bonding of Ti or stainless steel hairy-shaped or mesh-screen shaped surface structures onto an exemplary composition of the invention, e.g., a Ti implant; as described in detail, below.
Figure 21:
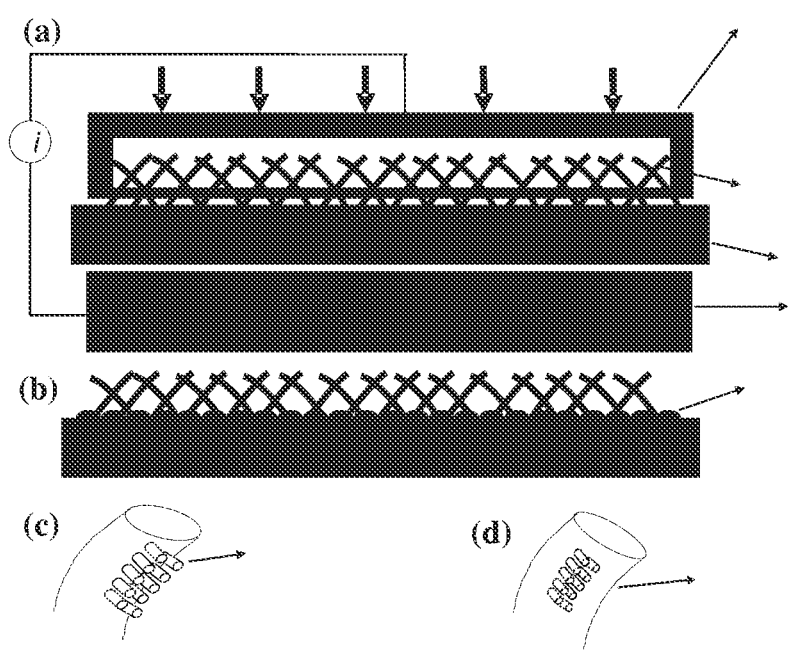
FIG. 21(a) to (d) illustrate an embodiment of the invention comprising spot-welding of Ti or stainless steel hairy-shaped or mesh-screen shaped surface structures onto an exemplary composition of the invention, e.g., a Ti implant; as described in detail, below.
Figure 22:
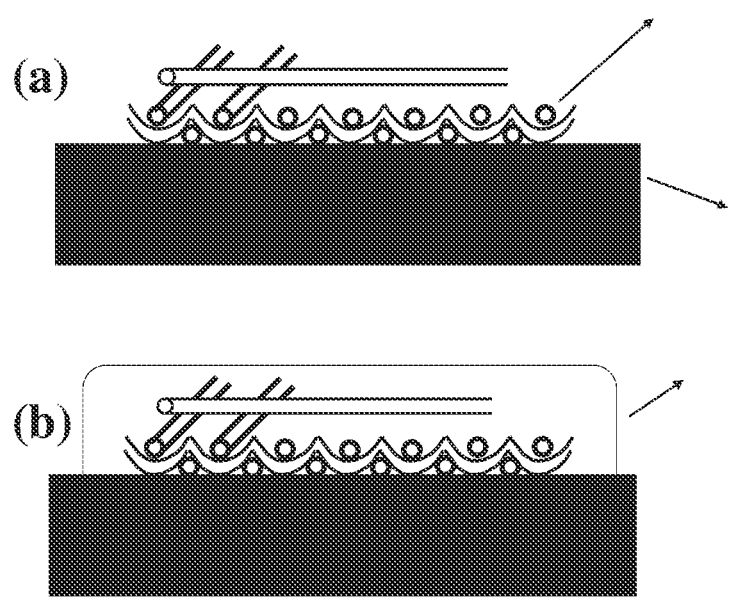
FIG. 22(a) and FIG. 22(b) illustrate an embodiment of the invention comprising exemplary $TiO_2$ nanotube or nanopore arrays; a side view of exemplary hairy-shaped or mesh-screen shaped surface structures are shown; as described in detail, below.

FIG. 17 illustrates exemplary $TiO_2$ nanotube or nanopore arrays on the surfaces of exemplary hairy-shaped, or mesh-screen-shaped Ti (or other biocompatible wire like stainless steel) bonded onto the Ti implant. Optionally, biological agents can be stored in the nanotubes or nanopores for growth factor, drug delivery, etc. FIG. 17(a) illustrates exemplary protruding (from the surface) $TiO_2$ nanotubes (left) and exemplary recessed (from the surface) $TiO_2$ nanotubes (right); wherein the illustrated example protruding structures comprising hairy or mesh screens Ti or other alloys are bent or angled to minimize tissue irritation (tissue or cell "poking"); the substrate upon which the nanotubes are fixed can also be made of Ti alloy or $TiO_2$. FIG. 17(b) illustrates an in vivo or in vitro environment with cell growth nutritional media (e.g., human or tissue culture medium), where cells, e.g., stem cells, chondrocytes, hMSCs or a mixture of chondrocytes and hMSCs, or any combination of cells; and in alternative embodiments the media comprises drugs, growth factors and/or antibiotics; FIG. 17(b) also illustrates how the invention can promote three-dimensional and geometrically secured cartilage growth around exemplary embodiments comprising e.g., compliant, hairy or spring-shaped Ti having nanotubes, e.g., $TiO_2$ nanotubes, or other nanostructures.

FIG. 18(a) illustrates an embodiment of the invention comprising exemplary $TiO_2$ nanotube or nanopore arrays; hairy-shaped or mesh-screen shaped surface structures; this exemplary structure comprises springy and compliant Ti microwires, e.g., 10 to 100 um in diameter; comprising on the wire surface (as the illustration highlight notes) $TiO_2$ nanotubes or nanopores, for e.g., large surface cell (e.g., stem cell or chondrocyte) growth and cartilage and/or ECM formation; in one embodiment this allows for "pseudo-vertical" growth of cartilage where spring wires are vertically enlongated. FIG. 18(b) schematically illustrates an embodiment of three-dimensional and geometrically secured cartilage growth around compliant spring-shaped Ti wires having $TiO_2$ nanotubes or other nanostructures.

FIG. 19(a) to (d) illustrate an embodiment of the invention comprising diffusional bonding of Ti hairy-shaped or Ti mesh-screen shaped surface structures onto an exemplary composition of the invention, e.g., a Ti implant; FIG. 19(a) illustrates an exemplary protruding structure comprising e.g., hairy or mesh screen wires, e.g., Ti wires on a Ti surface; FIG. 19(b) illustrates an embodiment comprising anchoring thick film Ti deposits; e.g., between about 100 to 2000 μm thick, optionally having an oblique incidence plus rotating substrate; FIG. 19(c) illustrates an embodiment comprising diffusion annealed and bonded Ti layer at e.g. between about 500 to 1000° C. for between about 0.1 to 100 hours; FIG. 19(d) illustrates an embodiment comprising both Ti wire surfaces and flat Ti surfaces anodized to have a (e.g., $TiO_2$) nanopore or nanotube structure.

FIG. 20(a) to (d) illustrates an embodiment of the invention comprising melt-bonding of Ti or stainless steel hairy-shaped or mesh-screen shaped surface structures onto an exemplary composition of the invention, e.g., a Ti implant. FIG. 20(a) illustrates an embodiment comprising heating of nanotubes or nanowires (which here comprise the protruding "hairy" or mesh screen shaped embodiments on a Ti base) by e.g. induction heating using radio frequency (RF) waves, electron-beam ("e-beam") heating, laser heating, torch heating and/or furnace heating; FIG. 20(b) illustrates the "melt-bonding" subsequent to the heating described in FIG. 20(a). FIG. 20(c) illustrates an embodiment comprising protruding $TiO_2$ nanotube structures on an exemplary wire surface made e.g., by anodization; and FIG. 20(d) illustrates an embodiment comprising recessed $TiO_2$ nanotube structures on an exemplary wire surface.

FIG. 21(a) to (d) illustrate an embodiment of the invention comprising spot-welding of Ti or stainless steel hairy-shaped or mesh-screen shaped surface structures onto an exemplary composition of the invention, e.g., a Ti implant. FIG. 21(a) illustrates an embodiment comprising spot welding of nanotubes or nanowires onto a base, e.g., a $TiO_2$ base, the circled "i" representing current running between an upper electrode and a lower electrode for compression spot welding. In alternative embodiments the spot welding upper electrode is in the shape of a disk, plate, grid, frame and the like. In alternative embodiments the upper electrode contact region is e.g., Au, Pt, Pd or an alloy of one or more of these Au, Pt, Pd or other metals. This illustration also includes protruding "hairy" or mesh screen Ti wires. FIG. 21(b) illustrates the spot welded Ti region subsequent to the welding described in FIG. 21(a). FIG. 21(c) illustrates an embodiment comprising protruding $TiO_2$ nanotube structures on an exemplary wire surface made e.g., by anodization; and FIG. 21(d) illustrates an embodiment comprising recessed $TiO_2$ nanotube structures on an exemplary wire surface.

FIG. 22(a) and FIG. 22(b) illustrate an embodiment of the invention comprising exemplary $TiO_2$ nanotube or nanopore arrays; a side view of exemplary hairy-shaped or mesh-screen shaped surface structures are shown. FIG. 22(a) illustrates an embodiment comprising spot welding, or induction melting-bonding, or electron-beam ("e-beam") bonding, or laser bonding, or a braze-bonded Ti wire mesh, e.g., as a single or a multi-layer) comprising a surface nanopore or nanotube array. In alternative embodiments the construction (e.g., as an implant) can be as a flat, round and/or curved surface, e.g., a Ti surface. FIG. 22(b) illustrates an embodiment comprising three-dimensionally secured cartilage growth around woven or compliant, gauze Ti wire mesh; in this embodiment the cartilage is "mechanically locked" onto the mesh and thus has enhanced toughness and strength.

In alternative embodiments, for the three-dimensional, wire-containing scaffold structures of the invention, e.g., as in the exemplary structures illustrated in FIG. 17 to FIG. 22, the springy and compliant metallic wires or microwires have a diameter in the range of e.g. between about 10 to 100 um in diameter. In alternative embodiments, these wires have a surface structure of nanostructures, e.g., nanotubes, nanowires, nanoribbons and/or nanopores for e.g., enhanced chondrocyte adhesion and cartilage growth, or for enhanced bone adhesion and growth.

In alternative embodiments, the material used for the three-dimensional springy, coil, wire, or mesh screen scaffold of FIGS. 17 to 22 comprises a metal or alloy selected from Ti, Zr, Hf, Nb, Ta, Mo or W, or alloys containing at least one of these elements, or stainless steel, or Co—Cr—Ni—Mo alloy (commonly known as MP35N alloy), or oxides comprising one of these elements or alloys, or any mixture thereof.

FIG. 23(a) FIG. 23(b) and FIG. 23(c) illustrate embodiments of the invention comprising exemplary flat or dual-structured Ti implants having compliant, three-dimensional wire assembly structure, as described in detail, below. FIG. 23(a) illustrates an embodiment comprising bonded protruding hairy or springy Ti wire or mesh with surface nanopores or nanowires (made e.g., of $TiO_2$) on a Ti flat surfaced base. FIG. 23(a) illustrates an embodiment comprising hairy or springy Ti wire or mesh with surface nanopores or nanowires (made e.g., of $TiO_2$) and a dual-structured macroscopically cell-locking or cartilage-locking (e.g., adhesion) surface (e.g., of an implant). FIG. 23(c) illustrates an embodiment comprising "bottle-necked" shapes, e.g., having constricted entrances, to slow and control release of compositions and/or material within the microscopic/macroscopic cavities/chambers on the implant surface; the compositions and/or material within the cavities/chambers can comprise proteins, growth factors, or antibiotics and the like. The "bottle-necked" shapes of the cavities/chambers also can facilitate having cells (e.g., stem cells, hMSCs, chondrocytes) adhere to the surface.

FIG. 24(a), FIG. 24(b) and FIG. 24(c) illustrate embodiments of the invention comprising exemplary $TiO_2$ compositions of the invention comprising Ti or Ti alloy particles or fibers. FIG. 24(a) illustrates an embodiment comprising protruding micro or macro particles or fibers (which can be Ti, Ti alloys or other material) as a cross-sectional view of the particles or fibers, attached on a Ti implant surface; which can be attached by e.g., induction melting-bonding, or electron-beam ("e-beam") melt bonding, or laser bonding, or spot welding, or braze bonding, etc. In alternative embodiments the construction (e.g., as an implant) can be as a flat, round and/or curved surface, e.g., a Ti surface. FIG. 24(b) illustrates an embodiment comprising surface-modified particles, e.g., Ti particles, of FIG. 24(a); which can be modified e.g. by anodization-induced modification of a $TiO_2$ nanotube or nanopore surface. FIG. 24(c) illustrates an embodiment comprising "locked in" bone and/or cartilage growth around and/or in Ti particles or fibers (which in different embodiments can be on a micro- and/or nano-scale size) using the exemplary embodiments described in FIG. 24(a) and FIG. 24(b).

Figure 25:
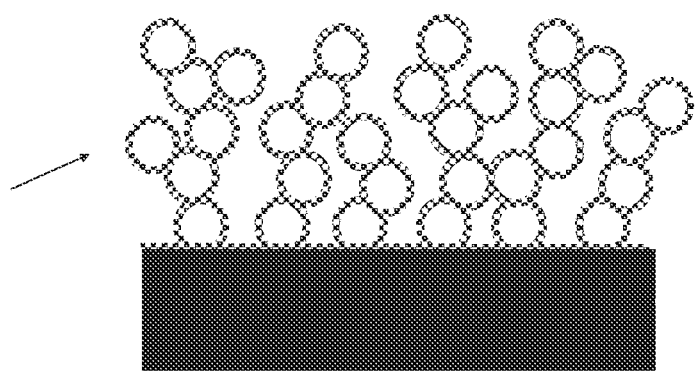
FIG. 25 illustrates an embodiment of the invention comprising sintering exemplary Ti or Ti alloy particles or fibers onto an exemplary composition of the invention, e.g., a Ti implant.

FIG. 25 illustrates an embodiment of the invention comprising sintering exemplary Ti or Ti alloy particles or fibers onto an exemplary composition of the invention, e.g., a Ti implant; where the arrow points to exemplary "protruding" surface-modified Ti particle aggregates, or exemplary "protruding" surface-modified Ti fiber aggregates; made e.g., using an anodization-induced $TiO_2$ nanotube or nanopore on the particle and/or fiber surface. This embodiment has the aggregates on a flat surface; but alternatively as with any surface of a composition of the invention, the surface also can be shaped in any way, e.g., round or curved.

FIG. 26(a), FIG. 26(b) and FIG. 26(c) illustrate embodiments of the invention comprising Ti or Ti alloy wire or ribbon arrays unidirectionally or vertically aligned, with the surface of wires or ribbons anodized to form $TiO_2$ nanotubes. FIG. 26(a) illustrates Ti wire or ribbons on a Ti base formed e.g., by bonding onto the Ti base surface, or etching onto the Ti base surface. FIG. 26(b) illustrates $TiO_2$ nanotube and/or nanopore arrays on the surfaces of the wires or ribbons. FIG. 26(c) illustrates that in this exemplary embodiment the chondrocyte or cartilage growth is guided somewhat vertically along the Ti wire or ribbon direction. In one embodiment the wires or ribbons are "compliant" on an implant surface for increased surface area and enhanced cell (e.g., stem cell, chondrocyte), cartilage and/or bone growth.

FIG. 27(a) and FIG. 27(b) illustrate embodiments comprising exemplary compositions of the invention comprising compliant, springy or bent Ti or Ti alloy wires, ribbons, columns, mesh screens or ribbon arrays on a Ti or Ti alloy base or surface. This embodiment has the aggregates on a flat surface; but alternatively as with any surface of a composition of the invention, the surface also can be shaped in any way, e.g., round or curved. In alternative embodiments, the FIG. 27(a) wires, mesh screens or ribbon arrays can be compliant, springy and/or bent, and can be Ti or Ti alloy, or $TiO_2$ or $TiO_2$ alloy, or a pure metal (e.g., Au, Pt, Pd) or a metal (e.g., Au, Pt, Pd) alloy. FIG. 27(b) illustrates an embodiment where a Ti mesh screen is bonded onto a Ti surface, e.g., an implant. FIG. 27(a) and FIG. 27(b) also illustrates an optional embodiment having spacers and/or "protectors" between sections of wires, ribbons, columns, mesh screens or ribbon arrays.

FIG. 28(a), FIG. 28(b) and FIG. 28(c) illustrate embodiments of the invention comprising exemplary compositions of this invention comprising nanotubes and/or nanopores on non-Ti surfaces such as ceramics, polymers, plastics and other non-Ti metals (e.g., Si, Au, Pt, Al) deposited or made by e.g., anodization. FIG. 28(a) illustrates an embodiment comprising "pre-patterned" a surface comprising a Ti or Ti alloy, or a pure metal (e.g., Au, Pt, Pd) or a metal (e.g., Au, Pt, Pd) alloy, or any mixture thereof; where in alternative embodiments the surface can have a "pre-patterned" regular or irregular shape. In alternative embodiments, a "pre-patterned" regular shape is made by machining or mask patterning. In alternative embodiments, a "pre-patterned" irregular shape is made by sandblasting or chemical etching. FIG. 28(b) illustrates an embodiment comprising a nanotube or nanopore layer on or within the surface of the product of manufacture of FIG. 28(a); in one embodiment this is made by depositing a Ti and/or Ti alloy on the surface and anodizing to make a nanotube and/or nanopore on or in the surface if the surface already does not comprise Ti or a Ti alloy. FIG. 28(c) illustrates the enhanced growth of cartilage and/or bone on the exemplary surfaces illustrated in FIG. 28(b) and FIG. 28(b).

Figure 28:
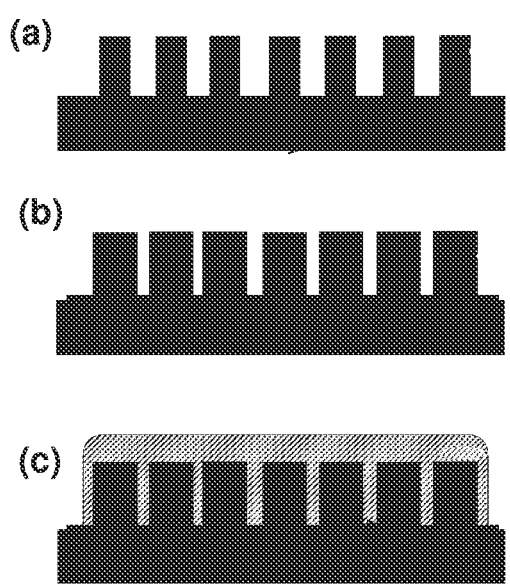
FIG. 28(a), FIG. 28(b) and FIG. 28(c) illustrate exemplary compositions of the invention comprising macroscopically enhanced Ti surfaces, as described in detail, below.

FIG. 29(a) and FIG. 29(b) illustrate embodiments of the invention comprising exemplary compositions comprising nanotubes and/or nanopores on non-Ti surfaces such as ceramics, polymers, plastics and other non-Ti metals (e.g., Si, Au, Pt, Al) deposited or made by e.g., anodization, as described above for FIG. 28. FIG. 29(a) illustrates nanotubes and/or nanopores on the surface of "lock-in" structures, which can be made as "pre-patterned" substrates, as described above for FIG. 28. FIG. 28(c) illustrates the enhanced growth of cartilage and/or bone on the exemplary surfaces.

It is understood that the above-described embodiments are illustrative of only a few of the many possible specific embodiments which can represent applications of the invention. Numerous and varied other arrangements can be made by those skilled in the art without departing from the spirit and scope of the invention. For example, in alternative embodiments of the invention the materials used to make the products of manufacture do not have to be Ti oxide nanotubes on Ti-based metals, as in alternative embodiments the nanotubes and nanopillars of this invention are adhered to other biocompatible materials, or non-biocompatible materials coated with biocompatible and bioactive surface layer, e.g., in an alternative embodiments a biocompatible surface layer comprises Ti, a portion of which can be converted into a $TiO_2$ nanotube, nanowire and/or nanopillar array configuration.

Kits

The invention provides kits comprising compositions of the invention (e.g., the products of manufacture of the invention, such as implants); and optionally also comprising materials for practicing methods of the invention, and optionally also comprises instructions for practicing the methods of this invention.

The invention will be further described with reference to the following examples; however, it is to be understood that the invention is not limited to such examples.

EXAMPLES

Example 1

The following examples describe $TiO_2$ nanotubes of the invention having various dimensions, and their fabrication; and demonstrate how they enhance chondrocyte growth and accelerate extracellular matrix formation.

Fabrication of Nanotube Array Structure for Chondrocyte Culture Experiments.

Shown in FIG. 2 are exemplary $TiO_2$ nanotube structures of the invention prepared for chondrocyte culture. Primary bovine cartilage chondrocyte (BCC) was utilized for the experiments. The vertically aligned $TiO_2$ nanotubule array structures with different nanotube diameters, as shown in the scanning electron microscopy photographs illustrated in FIG. 2, were fabricated by anodization technique using a Ti sheet (0.25 mm thick, 99.5% purity) which is electrochemically processed in a 0.5% HF solution at 20, 15, 10, or 5 V for 30 min at room temperature. A platinum electrode (thickness: 0.1 mm, purity: 99.99%) was used as the cathode. To crystallize the as-deposited, amorphous-structured $TiO_2$ nanotubes into the desired anatase phase, the specimens were heat-treated at 500° C. for 2 hrs. In this application, it is preferred that the amorphous $TiO_2$ nanotubes is crystallized to anatase phase by heat treatment, because an amorphous $TiO_2$ phase tends to be more susceptible to breakage by external stresses as compared to a crystalline phase.

The SEM images illustrated in FIG. 2 show highly ordered nanotubes with four different pore sizes between 30-100 nm created by controlling potentials ranging from 5 to 20V. The geometrical features used for the chondrocyte culture were 30, 50, 70, 100 nm diameter titania ($TiO_2$) nanotubular surfaces prepared by anodization. The height of the nanotubes was in the range of ~250-300 nm. The dimensions of the nanotubes were varied in order to determine how the size of the nanotubes influences the chondrocyte behavior as previous studies have shown for other types of cells, e.g., see Park (2007) Nano Lett. 7(6):1686-1691.

Chondrocyte Culture and SEM Analysis of Cell Morphology

Figure 7:
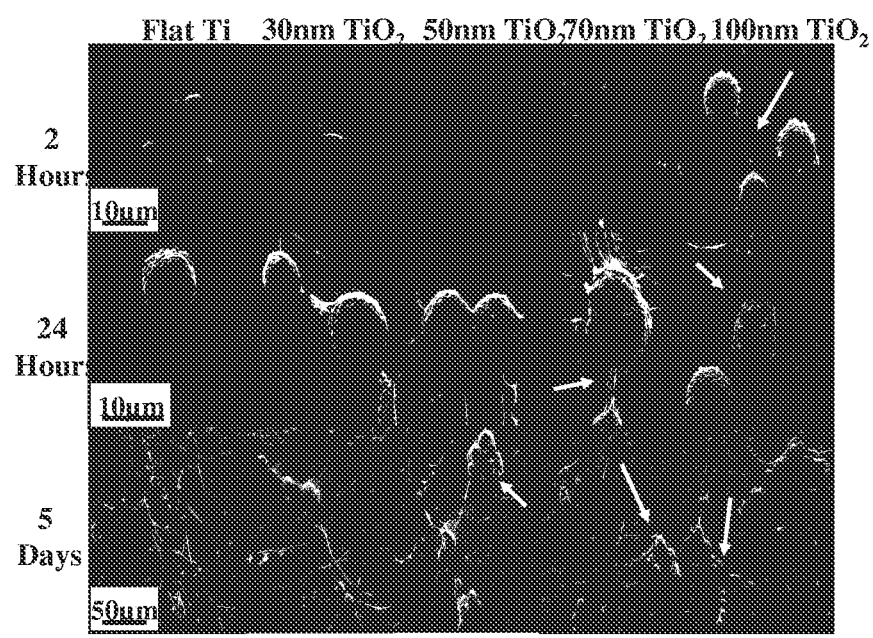
FIG. 7 illustrates fifteen panel images of SEM micrographs of bovine cartilage chondrocytes (BCCs) on flat Ti and 30, 50, 70, 100 nm diameter $TiO_2$ nanotube surfaces of this invention after 2 hours (top row), 24 hours (middle row), and 5 days (lower row) of culture. Arrows indicate difference in ECM fibril formation and cell clustering on the nanotube substrates, seen in larger diameters (70 and 100 nm), compared to flat Ti; as described in detail, below.

FIG. 7 shows comparative SEM images of bovine cartilage chondrocytes (BCCs) cultured 2 hours, 24 hours, and 5 days on flat Ti vs. different diameter (30, 50, 70, 100 nm) on exemplary $TiO_2$ nanotube surfaces. At 2 hours (FIG. 7 top row), chondrocytes initially appear like they are beginning to spread out on all surfaces (indicated by the ring of dark conceivable matrix like material surrounding the cells) except for the 100 nm $TiO_2$ nanotube surface. Uniquely, the cells on the nanotubes with the large 100 nm pores remain spherical on the surface having no dark surrounding material deposition. Unlike any other surface, cells on the 100 nm diameter $TiO_2$ nanotubes elicit extracellular matrix (ECM) fibrils (arrow) forming inter-cellular bridges between adjacent chondrocytes at the very early time point of 2 hours of culture incubation.

At 24 hours of culture (FIG. 7 middle row), the chondrocytes on the exemplary Ti substrate continue to show signs of possible flattening and spreading on the surface indicated by the dark matrix areas on the periphery of the cells. On the exemplary nanotube surfaces however, flattening has been reduced and much increased ECM fibrils are present (arrows), especially on the 70 nm and 100 nm pore size nanotubes. The nanotubes substrates appear that they are inducing a positive response from the chondrocytes because it is observed that the cells begin initiating ECM deposition and fibril organization within the initial 24 hours of culture.

Figure 8:
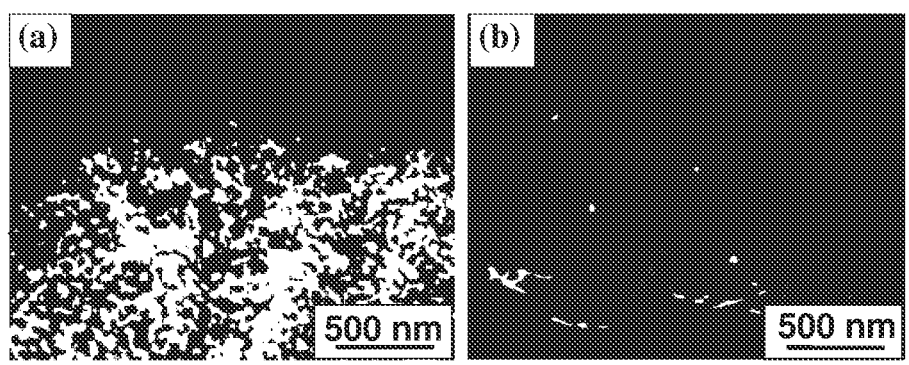
FIG. 8(a) and FIG. 8(b) illustrate higher magnification SEM observations of bovine cartilage chondrocytes (BCCs) reveal a striking difference in the formation of ECM (see arrow) between the flat Ti surfaces, as illustrated in FIG. 8(a) versus surfaces of an exemplary nanotube structure as illustrated in FIG. 8(b), after 24 hours of culture; as described in detail, below.

Higher magnification SEM observations of BCCs (24 hours of culture) in FIG. 8 reveal a striking difference in the formation of ECM between the flat Ti (as illustrated in FIG. 8(a)) vs. nanotube (30 nm diameter $TiO_2$ nanotubes shown in this image) (as illustrated in FIG. 8(b)) surfaces. There is a deposition of dense, fibril material on the nanotubular surfaces of this invention as illustrated in FIG. 8(b), most likely collagen Type II, a primary ECM molecule produced by chondrocytes and a ground substance in cartilage tissue. It appears that the nanotubes are actually regulating the cells by facilitating a more intricate, nanoscale order of ECM deposition. The nanotopography supports ECM molecule distribution atop the walls of the nanotubes of this invention, allowing for a type of guidance of fibril formation.

By contrast, the ECM deposited upon the flat Ti surface (as illustrated in FIG. 8(a)) is irregular, sparse, and thus lacks surface structuring cues for signaling ECM fibril organization. Moreover, it could be that fibers of bio active material such as collagen in this case are "nano-inspired" to form on the nanotube structure of this invention because of the fine scale cues and top surface (tip of the vertical wall) of $TiO_2$ nanotubes having a physically confined geometry which could aid in fibril formation. It was demonstrated previously that the nanotubes produced bio-active nanostructured formations of sodium titanate nanofibers on the top of $TiO_2$ nanotubes when nanotubes were exposed to the NaOH solution, see e.g., Oh (2005) Biomaterials 23:2945-2954.

With increased ECM production as seen in the SEM micrographs at early time points (2 and 24 hours), nanotubes most likely promote the proper ECM structuring of molecules much faster and more efficiently than the flat substrate of Ti. In addition, the naturally present pore configuration within the nanotubes can possibly be utilized as nano-depots to store and entrap extra biomolecules and nutrients while the fluid spaces in-between the nanotube walls allow for the exchange of gas, nutrients, and cell signaling molecules for an overall enhanced cell environment. The increased surface area with 100 nm diameter $TiO_2$ nanotubes having approximately 20× the amount of surface area compared to flat Ti quite possibly increases the ECM storage capacity.

At even longer culture times of 5 days, the chondrocytes on the nanotube structures appear to be encased in think beds of extracellular matrix FIG. 7 (bottom row). The arrows indicate a type of cell cluster formation within ECM beds that seem to link the cells together, connecting long strings of chondrocytes. Flat Ti had less cell clusters and more fibroblastic or elongated type cells spread over a large area where more cells on the nanotube substrates seemed to be spherical, retaining the phenotypical chondrocyte shape. In one aspect, the nanotube geometry seen in FIG. 2 can aids in preserving this morphology because of the distinct structure of the surface, where cells may be localized atop the pores, anchored possibly and confined by the tube contour. The chondrocytes on the flat Ti seem to spread along the surface probably because the necessary structuring cues and nanopores needed for shape confinement are absent.

Cell Viability

Figure 9:
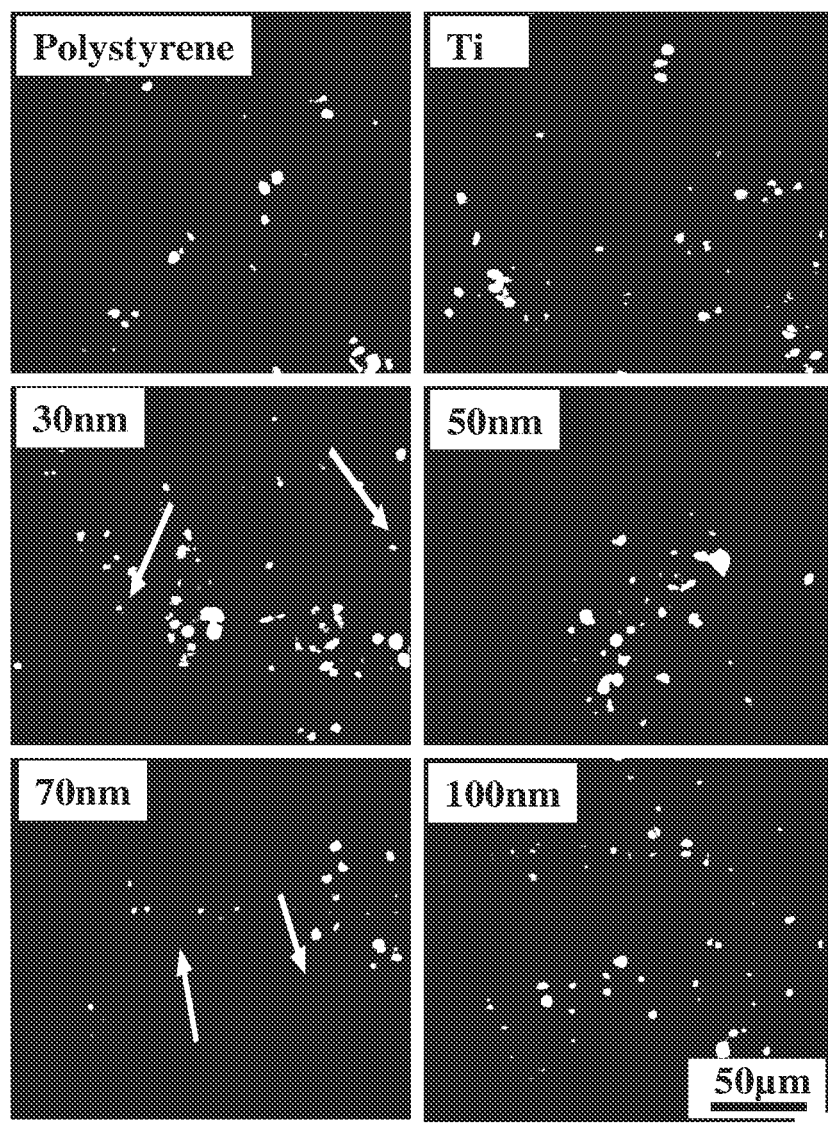
FIG. 9 schematically illustrates six panels of immunofluorescent images of cells grown on exemplary compositions of this invention (having nanotube surfaces) to show the viability of bovine cartilage chondrocytes (BCCs) using fluorescein diacetate (FDA) cytoplasmic staining (a viability-staining technique); the cells were cultured for 5 days on control polystyrene culture dishes, flat Ti and 30, 50, 70, 100 nm diameter $TiO_2$ nanotube surfaces of this invention; viability-staining demonstrates that practically all the cells were alive on all surfaces; as described in detail, below.

In order to show the viability of chondrocytes on the substrates, chondrocytes on control polystyrene (Nunc 12-well plate), flat Ti, and 30, 50, 70, 100 nm $TiO_2$ nanotube substrates were incubated with fluorescein diactate (FDA) cytoplasmic fluorescent dye after 5 days of culture. The FDA (green fluorescence) images are illustrated in the panels of FIG. 9. More notably round shaped cells were observed on the nanotube substrates while more cell flattening and fibroblastic shaped cells were apparent on the polystyrene and Ti surfaces comparatively. This flattening may indicate loss of the chondrogenic phenotype on polystyrene and Ti.

FIG. 9 schematically illustrates six panels of immunofluorescent images of cells grown on exemplary compositions of this invention (having nanotube surfaces) to show the viability of bovine cartilage chondrocytes (BCCs) using fluorescein diacetate (FDA) cytoplasmic staining (a viability-staining technique); the cells were cultured for 5 days on control polystyrene culture dishes, flat Ti and 30, 50, 70, 100 nm diameter $TiO_2$ nanotube surfaces of this invention; viability-staining demonstrates that practically all the cells were alive on all surfaces, as described in detail, below.

Cell Shape Analysis

Figure 10:
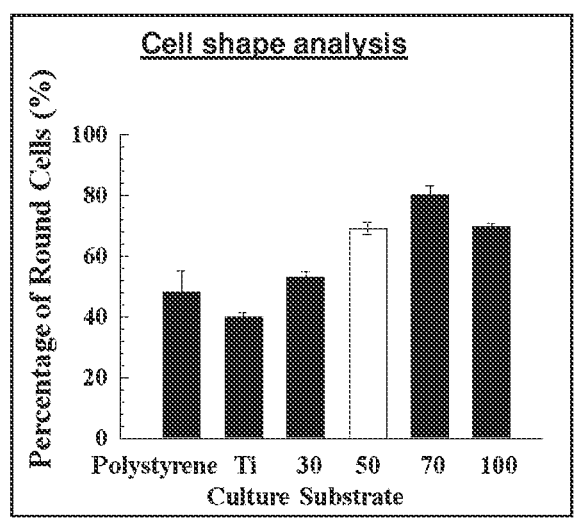
FIG. 10 schematically illustrates in bar graph form a summary of data of bovine cartilage chondrocyte (BCC) cell shape analysis based on fluorescein diacetate (FDA) viability staining; the bar graph shows the average percentage of round cells±standard error bars; larger diameter exemplary nanotubes show significantly larger percentages of round cells over polystyrene and flat Ti controls; this demonstrates that the nanotubes of this invention preserve the spherical phenotypic shape of the chondrocytes more efficiently; as described in detail, below.

The morphological analysis based on the FDA observations, as graphically illustrated in FIG. 10, may further imply that the nanotubes induce a more spherical chondrocyte shape. The percentage of round cells was significantly lower for bovine cartilage chondrocytes (BCCs) on the polystyrene, Ti, and the smallest diameter (30 nm) nanotube substrates compared to the 50 nm, 70 nm, and 100 nm $TiO_2$ nanotube surfaces. The highest percentage of round cells on the 70 nm pore size sample reached approximately 80%.

Functional Inspection: Extracellular Matrix (ECM) Formation

Cartilage consists of two main components, chondrocyte cells and their matrix. The structure of the matrix is composed of two basic macromolecules that are essential for the structural and functional integrity of cartilage, namely type II collagen and aggrecan, see e.g., Muir, H., *The chondrocyte, architect of cartilage. Biomechanics, structure, function and molecular biology of cartilage matrix macromolecules.* Bioessays, 1995. 17(12): p. 1039-48. Aggrecan consists of both a core protein and keratin sulfate glycosaminoglycan (GAG) chains which fill the narrow spaces within the collagen, see e.g., Muir (1995) supra.

Figure 11:
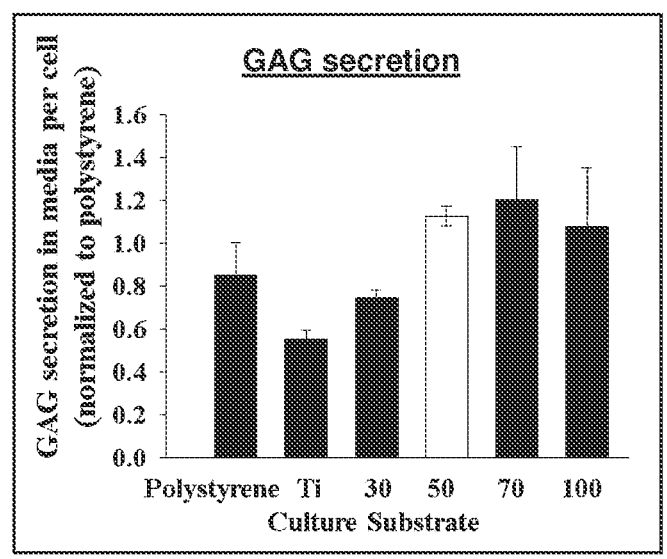
FIG. 11 schematically illustrates in bar graph form a summary of data of glycosaminoglycan (GAG) secretion (relative to that measured in control culture dish) in the media in contact with flat control surface (polystyrene) and exemplary 30, 50, 70, 100 nm diameter nanotube substrates (nanotube substrata±SEM); as described in detail, below.

In FIG. 11, the glycosaminoglycan (GAG) amount secreted in the media in contact with the different substrates was evaluated relative to control polystyrene culture dishes. Clearly, the nanotubular surfaces of this invention up-regulate GAG secretion. There is a general trend that shows increasing amounts of GAG secretion with increasing size of nanotube diameter, reaching its highest at approximately 70 nm diameter, with twice as much GAG secreted in the media compared to flat Ti (the Ti surface is covered with thin native $TiO_2$ oxide layer). While the exact mechanism is yet to be thoroughly understood, and the invention is not limited by any particular mechanism of action, the nanotube functionality trend is likely due to the slight change in cytoskeletal tension and focal adhesion distances due to pore size of the nanotubes.

Naturally, aggrecan draws water into the tissue and swells against the collagen network, thereby resisting compression and allowing for proper joint movement, see e.g., Muir (1995) supra. While the invention is not limited by any particular mechanism of action, in some aspects the up-regulation of GAG chains is indicative of the increased aggrecan production observed on the larger sized nanotube pores in exemplary structures of this invention; and this could imply that because there are increased storage volume capabilities as pore size increases it triggers a higher rate of production because the molecule retention ability of the cellular environment has been inflated.

Figure 12:
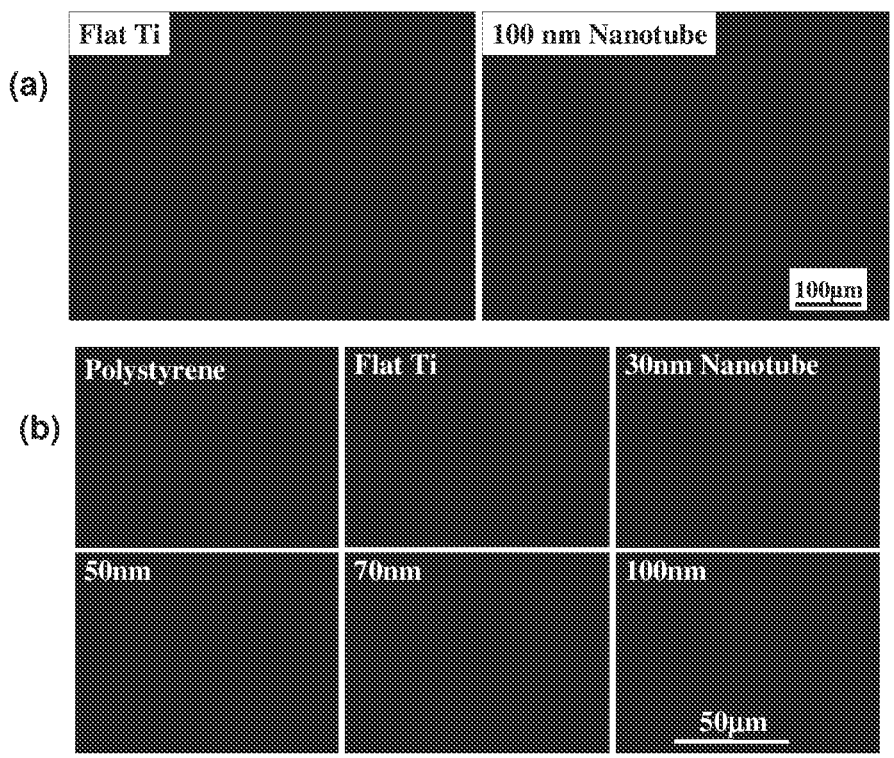
FIG. 12 illustrates immunofluorescent images of collagen type II (red) ECM fibrils produced by bovine cartilage chondrocytes (BCCs)

To further evaluate the response of BCCs for this comparative surface morphology, the functional modification of collagen type II expression by the different surface physiological conditions was also measured. Comparative immunofluorescent images of collagen type II ECM fibrils produced by BCCs on flat Ti vs 100 nm diameter $TiO_2$ nanotube surfaces are illustrated in FIG. 12(a). We observed an up-regulated collagen type II expression on the nanotube surface where fibrils have formed intricate networks connecting cells over a long range order which is basically absent on the Ti surface. The images in FIG. 12(b) represent higher magnification immunofluorescent images of collagen type II (red) and DAPI (blue) nuclear staining of BCCs on polystyrene, flat Ti, and 30, 50, 70, 100 nm TiO$_2$ nanotube surfaces after 5 days of culture.

Large aggregates and cell assemblies expressing collagen type II are seen on the nanotube surfaces. In a similar trend as the GAG secretion, as nanotube size generally increased, the collagen production and network activation between cells increased (data not shown). The collagen type II expression on the nanotube surface also reveal dense beds and clusters of ECM structures and lacunae type structures possibly mimicking the natural matrix cavities in an actual cartilage environment. While the invention is not limited by any particular mechanism of action, the nanotubes of the products of manufacture of the invention may be facilitating a more natural and active response of BCCs.

The results obtained demonstrate that the presence of the nanotube structures of this invention significantly up-regulate glycosaminoglycan (GAG) secretion and collagen Type II production by chondrocytes, which is beneficial for cartilage repair. It was found that increasing the diameter of the nanotubes to the approximate regime of 70 nm to 100 nm in this invention increased the cartilage related productivity. Nanotube diameter sizes larger than 100 nm can also be used, and these larger sizes, to some extent, may also increase the productivity threshold as compared with an implant surface with no nanotube structure.

A number of embodiments of the invention have been described. Nevertheless, it will be understood that various modifications may be made without departing from the spirit and scope of the invention. Accordingly, other embodiments are within the scope of the following claims.

What is claimed is:

1. A product of manufacture comprising:
   a plurality of nanotubes on a Ti and/or Ti-comprising alloy, or on a Ti-coated or Ti alloy-coated surface, or on a TiO$_2$ and/or TiO$_2$ alloy surface or coating, and
   a plurality of chondrocytes,
   wherein the nanotubes comprise a metal and/or a metal alloy comprising a Ti and/or an oxide of a Ti, and have a diameter of between about 50 to 100 nm,
   wherein the Ti and/or Ti-comprising alloy or the TiO$_2$ and/or TiO2 alloy surface or coating, or the Ti-coated or Ti alloy-coated surface, comprises one or more surfaces or a subsurface or a partial surface of the product of manufacture.

2. The product of manufacture of claim 1, wherein the product of manufacture comprises:
   (a) a thin coating of a metal, a metal oxide, and/or an alloy at least about 1, 2, 3, 4, 5, 10, 15 nm, 20 nm, 30 nm, 40 nm, 50 nm, 60 nm, 70 nm, 80 nm, 90 nm or 100 nm or more nm in thickness at the surface, and/or
   (b) at least a portion of the surface underneath comprises a vertically aligned and adhering nanotube, nanoribbon, nanowire and/or nanopillar array structure or structures, and/or a plurality of recessed nanopore or nanodepot structures.

3. The product of manufacture of claim 2, wherein the entrance dimension of the nano-depot, nanotube and/or nanopore is reduced or constricted or impeded by a selective deposition of a metal or an alloy, a metal oxide and/or alloy oxide, and/or another compound, to induce a partial bottle-necking or constricting configuration to slow down or impede the release rate of a compound or a substance stored in the nano-depot, nanotube and/or nanopore,
   wherein optionally the compound or substance comprises a drug and/or a biological agent stored in the nano-depot, nanotube and/or nanopore,
   wherein optionally the slowing down or impeding of the release rate of the compound or a substance stored in the nano-depot, nanotube and/or nanopore is at least by a factor of 2 or 3 or slower, or at least by a factor of about 10 or slower, than the case of non-bottlenecked or non-constricted structure,
   wherein optionally the other compound used to partially bottleneck or constricted or impeded the nano-depot and/or nanopore comprises a nitride, a fluoride, a carbide and/or a polymer material,
   wherein optionally the product of manufacture surface has a multiplex and/or a duplex distribution of nanostructure structures with different dimensions such that the product of manufacture comprises both one or more nano-depot, nanotube and/or nanopore structures having bottle-necked or constricted or impeded pore structures together with nano-depot, nanotube and/or nanopore structures which do not have the bottleneck diameter or constricted or impeded opening reductions,
   wherein optionally the relative area fraction of bottle necked or constricted or impeded opening nano-depot, nanotube and/or nanopore structures in the product of manufacture is in the range of about 2% to 50% of the total available surface area of the product of manufacture, or in the range of about 2% to 50% of the total available surface area available for stimulating cell growth, cartilage growth and/or bone deposition.

4. The product of manufacture of claim 1, wherein the product of manufacture further comprises a chemical, a drug and/or a biological agent,
   and optionally the chemical, drug and/or biological agent comprises a small molecule, a growth factor, a collagen, a protein, a biomolecule, a gene, a nucleic acid, an RNA or a DNA, a nucleic acid expression vector, an antibiotic, a hormone, a therapeutic drug, a functional particle, a liposome, or a magnetic, metallic, ceramic or a polymer particle; or, a differentiation-inducing chemical, drug and/or biomolecule,
   and optionally the chemical, drug and/or biological agent is attached to or coated on the product of manufacture, or is stored in a nanopore, nanodepot and/or nanotube, or the chemical, drug and/or biological agent is attached to, coated on or stored between a plurality of nanopillars, nanotubes, nanowires and/or nanoribbons,
   and optionally the chemical, drug and/or biological agent comprises a fibroblast growth factor (FGF), an epidermal growth factor (EGF), a vascular endothelial growth factor (VEGF), a transforming growth factor beta-1 (TGF-β1) or a transforming growth factor beta-2 (TGF-β2), a bone morphogenic protein (BMP), an agent that stimulates chondrocyte growth, maintenance and/or differentiation, a chemical or biomolecule osteogenic-inducing agent, a fibroblast growth factor and/or a vascular endothelial growth factor, a bisphosphonate, a chemical agent that suppresses the bone loss by suppressing osteoclasts,
   wherein optionally the chemical, drug and/or biological agent are positioned on the side of an implant surface intended for cartilage growth and comprise chondrogenic inducing agents, and/or a chemical or a biomolecule-comprising agent that stimulates chondrocyte growth, maintenance and/or differentiation;
   and optionally a biological agent positioned on another or opposite side of the implant surface is intended for bone growth and optionally comprises a chemical, drug and/or biological agent that stimulates or maintains bone growth;

wherein optionally the bone morphogenic protein (BMP) is bone morphogenetic protein 2 (BMP-2), bone morphogenetic protein 3 (BMP-3), bone morphogenetic protein 4 (BMP-5), bone morphogenetic protein 5 (BMP-5), bone morphogenetic protein 6 (BMP-6), bone morphogenetic protein 7 (BMP-7), bone morphogenetic protein 8 (BMP-8a), bone morphogenetic protein 10 (BMP-10), and/or bone morphogenetic protein 15 (BMP-15).

5. The product of manufacture of claim 4, wherein the functional particles comprise magnetic oxide particles or metallic particles utilized for remotely actuated RF heating and creation of temperature gradient for accelerated or switch-on, or switch-off release of the chemical, drug and/or biological agent stored in the nanodepot space.

6. A patch bone implant piece comprising a product of manufacture of claim 1, wherein optionally the product of manufacture serves a dual purpose of comprising at least one exposed surface comprising the plurality of chondrocytes, wherein the exposed surface enhances chondrocyte growth and cartilage formation, and an opposing surface or a bottom surface facing existing bone to induce a strong osseo-integration of the patch bone implant piece.

7. An implant, or a bone implant, or a patch implant, comprising a product of manufacture of claim 1.

8. A chondrocyte cell culture substrate for new chondrocyte production comprising the product of manufacture of claim 1.

9. The product of manufacture of claim 1, wherein the product of manufacture is an implant.

10. The product of manufacture of claim 1, wherein the nanotubes further comprise a metal and/or a metal alloy comprising a Zr, a Hf, a Nb, a Ta, a Mo and/or a W, or an oxide of a Zr, a Hf, a Nb, a Ta, a Mo and/or a W.

11. The product of manufacture of claim 1, wherein the nanotubes are formed directly and/or indirectly on and/or attached to a Ti surface and/or a Ti-coated surface, or Ti oxide surface and/or a Ti oxide-coated surface.

12. The product of manufacture of claim 1, wherein the nanostructures have a height dimension in the range of between about 30 to 10,000 nm.

13. The product of manufacture of claim 1, wherein the nanostructures have a thickness of between about 200 to 2,000 nm, or between about 200 to 500 nm thickness.

14. The product of manufacture of claim 1, wherein the Ti surface and/or Ti-coated surface, or Ti oxide surface and/or a Ti oxide-coated surface, comprises at least in part: a wire or microwire; a springy and/or a hairy wire or microwire; a mesh or mesh screen; a "pre-patterned" and/or a "pre-etched" surface made by machining or mask patterning and/or etching of the surface of the product of manufacture structure.

15. The product of manufacture of claim 14, wherein the wire comprises a three-dimensional Ti wire or microwire between about 10 to 100 μm in diameter and/or the Ti wire or microwire is a springy and compliant wire or microwire.

16. The product of manufacture of claim 14, wherein a material used for the three-dimensional springy, coil, wire, or mesh screen scaffold comprises at least one of a metal or an alloy selected from the group consisting of Ti, Zr, Hf, Nb, Ta, Mo and W, or an alloy or an oxide or a mixture thereof, or stainless steel, or a Co—Cr—Ni—Mo alloy (commonly known as MP35N alloy), wherein optionally the Ti or Ti oxide alloy or Ti or Ti oxide on the Ti-coated, or Ti oxide-coated or Ti alloy-coated surface is between about 100 to 2000 μm thick.

17. The product of manufacture of claim 1, wherein the product of manufacture structure comprises:

(i) oxides of alloys comprising Ti or a Ti oxide or a $TiO_2$ by at least about 5%, 10%, 20%, 30%, 40%, 50%, 60%, 70%, 80% or 90% or more in weight %, (ii) oxides of alloys comprising Zr, Hf, Nb, Ta, Mo, W, by at least about 5%, 10%, 20%, 30%, 40%, 50%, 60%, 70%, 80% or 90% or more weight %, or (iii) a ceramic, a polymer, a plastic, a Si-comprising composition, a Au-comprising composition, a Pd-comprising composition, a Pt-comprising composition, or a stainless steel.

18. The product of manufacture of claim 1, wherein the plurality of chondrocytes comprise an autologous chondrocyte, a hypertrophic chondrocyte, or a human chondrocyte.

19. The product of manufacture of claim 1, having a structure as illustrated in any one of FIGS. 16 to 29.

20. The product of manufacture of claim 1, wherein the product of manufacture further comprises a colony-forming unit-fibroblast (CFU-F), a marrow stromal cell, a stem cell, a totipotent cell, a multipotent progenitor cell and/or a pluripotent cell, wherein optionally the cell is implanted in, seeded in or placed in the product of manufacture in-vivo, in-vitro, and/or ex-vivo, and optionally the stem cell is a mesenchymal stem cell (MSC), an adult stem cell, an induced pluripotent stem cell (iPS cell or iPSC) and/or an embryonic stem cell.

21. The product of manufacture of claim 1, wherein the product of manufacture further comprises on a surface of the product of manufacture a nano-depot, a microcavity and/or a macrocavity comprising a cell, a drug and/or a biological agent, wherein optionally the nanotube or a nanopillar, or microcavity and/or a macrocavity, acts as a depot or storage area comprising a cell, a drug and/or a biological agent, and optionally the microcavity has an entrance dimension of between about 1 to 100 micrometer, or a macrocavity having an entrance dimension of between about 100 to 1,000 micrometer.

* * * * *